(12) United States Patent
Oeffinger et al.

(10) Patent No.: US 12,290,577 B2
(45) Date of Patent: May 6, 2025

(54) METHOD OF FREEZE DRYING SURFACTANT-STABILIZED MICROBUBBLES

(71) Applicants: Thomas Jefferson University, Philadelphia, PA (US); Drexel University, Philadelphia, PA (US)

(72) Inventors: Brian Edward Oeffinger, Philadelphia, PA (US); Margaret A. Wheatley, Media, PA (US); Rawan Shraim, Philadelphia, PA (US); Purva Vaidya, Flushing, NY (US); John Robert Eisenbrey, Wayne, PA (US)

(73) Assignees: Thomas Jefferson University, Philadelphia, PA (US); Drexel University, Philadelphia, PA (US)

( * ) Notice: Subject to any disclaimer, the term of this patent is extended or adjusted under 35 U.S.C. 154(b) by 298 days.

(21) Appl. No.: 17/810,157

(22) Filed: Jun. 30, 2022

(65) Prior Publication Data
US 2023/0044615 A1    Feb. 9, 2023

Related U.S. Application Data

(62) Division of application No. 16/817,898, filed on Mar. 13, 2020, now Pat. No. 11,389,552.

(60) Provisional application No. 62/817,886, filed on Mar. 13, 2019.

(51) Int. Cl.
*A61K 49/22* (2006.01)
(52) U.S. Cl.
CPC .......... *A61K 49/223* (2013.01); *A61K 49/227* (2013.01); *A61K 2800/84* (2013.01)
(58) Field of Classification Search
None
See application file for complete search history.

(56) References Cited

U.S. PATENT DOCUMENTS 9,700,640 B2   7/2017   Wheatley et al.
2016/0059036 A1   3/2016   Eisenbrey et al.

OTHER PUBLICATIONS

Albala, L., et al., "Preservation of imaging capability in sensitive ultrasound contrast agents after indirect plasma sterilization", International Journal of Pharmaceutics 494, 2015, 146-151.
Eisenbrey, J. R., et al., "Development of an ultrasound sensitive oxygen carrier for oxygen delivery to hypoxic tissue", International Journal of Pharmaceutics 478, 2015, 361-367.
Eisenbrey, J. R., et al., "Sensitization of Hypoxic Tumors to Radiation Therapy Using Ultrasound-Sensitive Oxygen Microbubbles", International Journal of Radiation Oncology Biology Physics, vol. 101, No. 1, 2018, 88-96.
Oeffinger, B. E., et al., "Preserving the Integrity of Surfactant-Stabilized Microbubble Membranes for Localized Oxygen Delivery", Langmuir 35, 2019, 10068-10078.
Solis, C., et al., "Preserving enhancement in freeze-dried contrast agent ST68: Examination of excipients", International Journal of Pharmaceutics 396, 2010, 30-38.
Wheatley, M. A., et al., "Comparison of in vitro and in vivo acoustic response of a novel 50:50 PLGA contrast agent", Ultrasonics 44, 2006, 360-367.

*Primary Examiner* — Jennifer Chin
(74) *Attorney, Agent, or Firm* — Saul Ewing LLP; Kathryn Doyle; Justin Crotty

(57) ABSTRACT

One aspect of the invention provides a method for freeze-drying surfactant-stabilized microbubbles. The method includes: preparing vials comprising a mixture comprising microbubbles; partially submerging the vials in a chilled water bath, wherein the water bath has a sub-freezing temperature; placing the vials on a cooled shelf of a lyophilizer; freeze-drying the vials in the lyophilizer; and capping the freeze-dried vials. Another aspect of the invention provides a method for annealing surfactant-stabilized microbubbles. The method includes: preparing vials comprising a mixture comprising microbubbles; passing the vials in and out of liquid nitrogen ($LN_2$) until the mixture is frozen; holding the vials at −20° C.; placing the vials on a cooled shelf of a lyophilizer; freeze-drying the vials in the lyophilizer; and capping the freeze-dried vials.

6 Claims, 19 Drawing Sheets

| Blue | Extrapol. Peak | 33.15 °C |
| | Peak Value | -0.28 mW |
| | Normalized | -29.28e-03 Wg^-1 |
| | Left Limit | 31.75 °C |
| | Right Limit | 34.28 °C |
| | Peak | 31.75 °C |
| Red | Extrapol. Peak | 32.41 °C |
| | Peak Value | -0.79 mW |
| | Normalized | -73.61e-03 Wg^-1 |
| | Left Limit | 31.39 °C |
| | Right Limit | 33.74 °C |
| | Peak | 31.79 °C |
| Black | Extrapol. Peak | 32.66 °C |
| | Peak Value | -2.07 mW |
| | Normalized | -0.24 Wg^-1 |
| | Left Limit | 31.02 °C |
| | Right Limit | 33.96 °C |
| | Peak | 31.02 °C |

| Blue | Extrapol. Peak | 52.18 °C |
| | Peak Value | -4.46 mW |
| | Normalized | -0.47 Wg^-1 |
| | Left Limit | 50.90 °C |
| | Right Limit | 53.11 °C |
| | Peak | 52.13 °C |
| Red | Extrapol. Peak | 51.77 °C |
| | Peak Value | -5.32 mW |
| | Normalized | -0.50 Wg^-1 |
| | Left Limit | 50.27 °C |
| | Right Limit | 53.84 °C |
| | Peak | 51.63 °C |
| Black | Extrapol. Peak | 51.37 °C |
| | Peak Value | -4.95 mW |
| | Normalized | -0.56 Wg^-1 |
| | Left Limit | 49.82 °C |
| | Right Limit | 53.79 °C |
| | Peak | 51.64 °C |

FIG. 15-2

METHOD OF FREEZE DRYING SURFACTANT-STABILIZED MICROBUBBLES

CROSS-REFERENCE TO RELATED APPLICATIONS

This application is a divisional application under 35 U.S.C. § 121 of U.S. patent application Ser. No. 16/817,898, filed Mar. 13, 2020 and issued as U.S. Pat. No. 11,389,552 on Jul. 19, 2022, which claims the benefit of priority under 35 U.S.C. § 119(e) from U.S. Provisional Patent Application Ser. No. 62/817,886, filed Mar. 13, 2019. The entire content of each of these applications is hereby incorporated by reference herein.

STATEMENT REGARDING FEDERALLY SPONSORED RESEARCH OR DEVELOPMENT

This invention was made with government support under grant number EB026881 awarded by the National Institutes of Health (NIH). The government has certain rights in the invention.

BACKGROUND OF THE INVENTION

Flash freezing reagents by immersing reagents contained in a glass vial into liquid nitrogen ($LN_2$), and freeze drying without first holding at $-80°$ C. is common practice. However, when this method is applied to freezing contrast agents, it does not produce echogenic bubbles. Microbubbles can be quite costly to prepare.

SUMMARY OF THE INVENTION

One aspect of the invention provides a method for freeze-drying surfactant-stabilized microbubbles. The method includes: preparing vials comprising a mixture comprising microbubbles; partially submerging the vials in a chilled water bath, wherein the water bath has a sub-freezing temperature; placing the vials on a cooled shelf of a lyophilizer; freeze-drying the vials in the lyophilizer; and capping the freeze-dried vials.

This aspect of the invention can have a variety of embodiments. The microbubbles can include SE61 microbubbles.

The mixture can further include a lyoprotectant. The lyoprotectant can include one or more selected from the group consisting of: sugar, polymer, surfactant, and combination thereof. The sugar can include one or more selected from the group consisting of: glucose, trehalose, sucrose, dextran and mannitol. The polymer can include one or more selected from the group consisting of poly(vinylalcohol) (PVA) and poly(vinylpyrrolidone) (PVP). The surfactant can include polyethylene glycol (PEG).

The vials can be partially submerged in the $-20°$ C. water bath for about 10 minutes. The vials can be partially submerged in the water bath until the mixture is frozen. The vials can be freeze-dried in the lyophilizer for 18 hours to 24 hours.

The cooled shelf can have a temperature of $-20°$ C. The water bath can have a temperature of $-20°$ C.

The microbubbles can remain in a liquid-crystalline phase during freeze-drying.

The microbubbles can have a core comprising oxygen

Another aspect of the invention provides a method for annealing surfactant-stabilized microbubbles. The method includes: preparing vials comprising a mixture comprising microbubbles; passing the vials in and out of liquid nitrogen ($LN_2$) until the mixture is frozen; holding the vials at $-20°$ C.; placing the vials on a cooled shelf of a lyophilizer; freeze-drying the vials in the lyophilizer; and capping the freeze-dried vials.

This aspect of the invention can have a variety of embodiments. The mixture can further include a lyoprotectant. The lyoprotectant can include one or more selected from the group consisting of: sugar, polymer, surfactant, and combinations thereof. The sugar can include one or more selected from the group consisting of: glucose, trehalose, sucrose, dextran and mannitol. The polymer can include one or more selected from the group consisting of poly(vinylalcohol) (PVA) and poly(vinylpyrrolidone) (PVP). The surfactant can include polyethylene glycol (PEG). The lyoprotectant can include a solution comprising about 1.8% glucose. The lyoprotectant can include a solution comprising about 5% glucose. The lyoprotectant can include a solution comprising at least about 5% glucose.

The microbubbles can include SE61 microbubbles.

The vials can be held at $-20°$ C. for a duration in the range of from 12 hours to 24 hours.

The cooled shelf can have a temperature of $-20°$ C.

The microbubbles can remain in a liquid-crystalline phase during freeze-drying.

The microbubbles can have a core including oxygen.

BRIEF DESCRIPTION OF THE DRAWINGS

The following detailed description of specific embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIG. 4A depicts exemplary temperature profiles of sample agents measured during the process of freezing in liquid nitrogen. FIG. 4B depicts exemplary dose response curves of resulting agents.

FIG. 5A depicts exemplary temperature profiles of agent samples measured during freezing. FIG. 5B depicts exemplary dose response curves of resulting agents.

FIG. 6A depicts exemplary temperature profiles of samples agents measured during freezing. FIG. 6B depicts exemplary dose response curves of resulting agents.

FIG. 9A illustrates SE61 in 1.8% (w/v) glucose-PBS showing product collapse. FIG. 9B illustrates SE61 in 5.0% (w/v) glucose-water showing an intact microbubble cake.

FIG. 11A illustrates overall curves showing the melt temperatures of the pure ice phase. FIG. 11B illustrates detailed portion showing the glass transition temperatures (Tg's) of the solutions, marked with stars.

FIG. 12A illustrates dose response and FIG. 12, FIG. 12B illustrates time response for $SE61_{O2}$ with 1.8% (w/v) glucose-PBS. FIG. 12C illustrates dose response and FIG. 12D illustrates time response for $SE61_{O2}$ with 1.8% (w/v) glucose-water. FIG. 12E illustrates dose response and FIG. 12F illustrates time response for $SE61_{O2}$ with 5.0% (w/v) glucose-water.

FIGS. 13-1 and 13-2 depicts flow cytometry representative data showing count density. Plots are forward scattering (FSC-A) vs side scattering (SSC-A) for SE61 at various times for the different processing conditions.

FIGS. 15-1 and 15-2 depicts a side-by-side comparison of differential scanning calorimetry curves of dried $SE61_{O2}$ with and without surfactant.

DETAILED DESCRIPTION OF THE INVENTION

Figure 1:
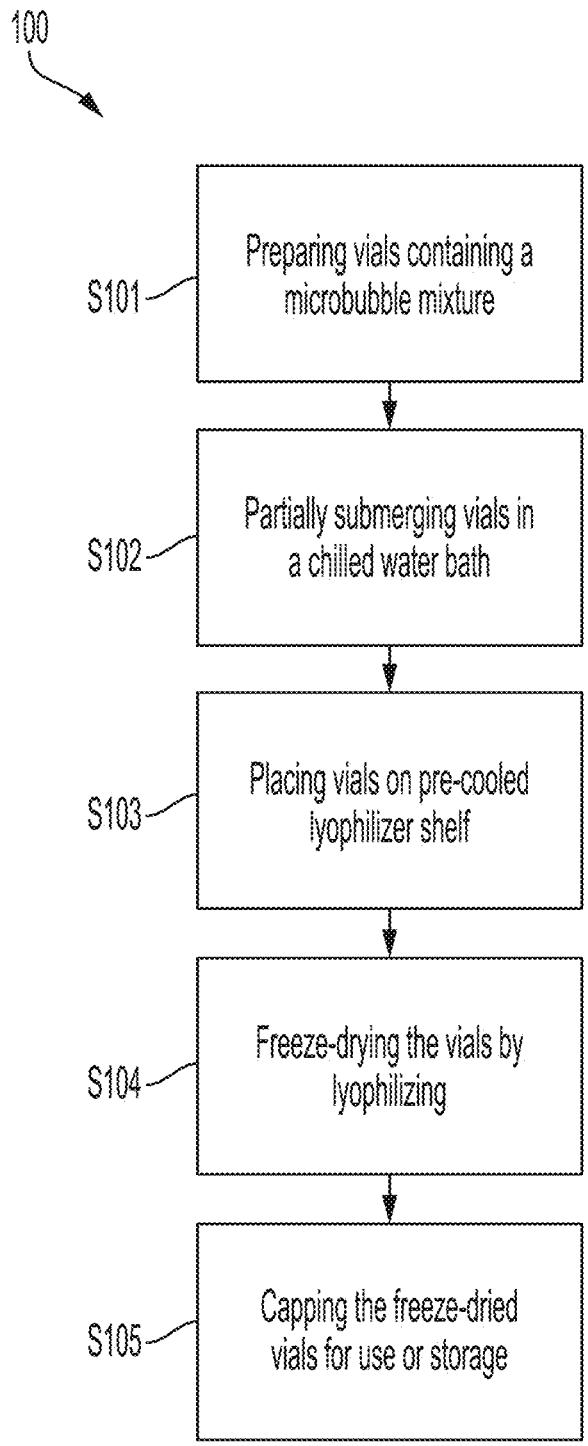
FIG. 1 depicts a schematic of an exemplary incremental rapid freezing method of the present invention.

The present invention provides methods for freeze-drying microbubbles such that the echogenicity of the microbubbles is preserved and their function as ultrasound contrast agents remains intact.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, specific materials and methods are described herein. In describing and claiming the present invention, the following terminology will be used.

It is also to be understood that the terminology used herein is for the purpose of describing particular embodiments only, and is not intended to be limiting.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DESCRIPTION

The present invention provides improved methods for freeze drying ultrasound contrast agents. The methods of the present invention may be applied to freeze drying microbubbles that can be used as both ultrasound contrast agents as well as therapeutic agents. The methods may be applied to microbubbles that have a surfactant shell with both a hydrophilic surface and a hydrophobic surface, and a gas core. The gas can be air, nitrogen, oxygen, nitric oxide, perfluorocarbon, sulfur hexafluoride, carbon dioxide and the like. The surfactant shell may include one or more encapsulated therapeutic agents.

Methods

The present invention provides improved methods for freeze drying contrast agents in order to retain their utility. The present invention is based on the discovery that freezing vials of contrast agents with small aliquots of liquid nitrogen ($LN_2$) poured over the vials, which slowed down the freezing rate, allowed the contrast agents to retain good maximum signal enhancement as compared to contrast agents that have been flash frozen. Accordingly, embodiments of the methods of the present invention include incrementally rapid freezing samples of contrast agents including surfactant-stabilized microbubbles. Embodiments of the methods of the present invention also include annealing surfactant-stabilized microbubbles.

Incremental Rapid Freezing

Embodiments of the present invention provide methods 100 for freeze-drying one or more samples of microbubbles using incremental rapid-freezing.

Referring now to FIG. 1, step S101 of method 100 may include first preparing vials containing a microbubble mixture. The vials may include any suitable vial as understood in the art, for example vials constructed from glass, cryoplastic, and the like. The vials may include vials having a volume of up to about 0.5 mL, about 1.0 mL, about 1.5 mL, about 2.0 mL, about 5 mL and the like.

Microbubbles

Embodiments of the microbubble mixture may include a volume of microbubbles including surfactant-stabilized microbubbles. Embodiments of the surfactant-stabilized microbubbles may include microbubbles formed from a combination of one or more surfactants including for example sorbitan monostearate (e.g., SPAN® 60, Sigma Aldrich) and d-alpha-Tocopheryl polyethylene glycol 1000 succinate (TPGS), designated SE61, and further described in U.S. Patent Application Publication Nos. 2016-0059036 and 2012-0237450. Embodiments of the microbubbles may be formed from one or more surfactants alone or in combination, including for example, TWEEN® (polysorbate) 80, TPGS, SPAN® 60, other sorbitan fatty acid esters, other sorbitan polyoxyethylene fatty acid esters, and the like. The microbubbles may include a gas-containing core, for example an oxygen ($O_2$) core. Embodiments of the microbubbles may include a gas core containing nitrogen, nitric oxide, carbon dioxide, perfluorocarbon, sulfur hexafluoride, octafluoropropane, air, perfluorohexane, or other suitable echogenic gas as understood in the art.

Lyoprotectants

The mixture may further include one or more lyoprotectants. The lyoprotectants may include glucose. In some embodiments, the glucose is dissolved in one or more aqueous solutions including for example, water, saline, buffered saline including phosphate buffered saline, and the like. The glucose may be dissolved in aqueous solution to a concentration of up to about 1.0%, about 1% to about 1.5%, about 1.5% to about 2.0%, about 2.0% to about 2.5%, about 2.5% to about 3.0%, about 3.0% to about 3.5%, about 3.5% to about 4.0%, about 4.0% to about 4.5%, about 4.5% to about 5.0%, about 5.0% to about 6.0%, and/or greater than about 6.0%. In some embodiments, the glucose may have a concentration of about 1.8%. In some embodiments, the glucose may have a concentration of about 5.0%. The glucose may be dissolved in an aqueous solution to a concentration of up to about 100 mM, about 100 mM to about 150 mM, about 150 mM to about 200 mM, about 200 mM to about 250 mM, about 250 mM to about 300 mM, and/or greater than about 300 mM. The lyoprotectants may include trehalose, sucrose, mannitol, inulin, dextran, one or more polymer-based lyoprotectants (e.g., poly(vinylalcohol) (PVA), poly(vinylpyrrolidone) (PVP) and the like), one or more surfactants such as polyethylene glycol (PEG), one or more bulking agents as understood in the art, and/or combinations thereof.

Embodiments of step S102 may include at least partially submerging one or more prepared vials into a chilled controlled environment, including for example, a chilled water bath and/or recirculating chiller bath. The chilled controlled environment (e.g., chiller bath having equal parts water and a refrigerant such as propylene glycol) may be chilled, with or without gentle shaking or swirling, while keeping the bubbles suspended during freezing, to a temperature of less than about −20° C., about −20° C. to about −25° C., about −25° C. to about −30° C., about −30° C. to about −35° C., and the like. The chilled controlled environment (e.g., chiller bath) may be chilled to a temperature of about −22° C. The vials may be at least partially submerged so that up to about 50% of the exterior surface of the vials is submerged in the chilled water bath. That is, the vials may be submerged so that the exterior of the vials are about 10% to about 20% submerged, about 20% to about 30% submerged, about 30% to about 40% submerged, or about 40% to about 50% submerged. The vials may be submerged so that more than 50% up to about 100% of the exterior surface of the vials are submerged in the chilled water bath. That is, the vials may be submerged so that the exterior of the vials are about 50% to about 60% submerged, about 60% to about 70% submerged, about 70% to about 80% submerged, about 80% to about 90% submerged, about 90% to about 100% submerged and/or about 100% submerged. In some embodiments, the chilled controlled environment may include, for example, a thermoelectric (Peltier) cooler, a thermocycler, and the like. The one or more prepared vials may be placed into the thermocycler and cooled to a temperature of about −20° C. The vials may be cooled to a temperature of about −15° C. to about −25° C., about −20° C. to about −30° C., and the like. In some embodiments, the prepared vials are chilled by one or more other means including, for example, a refrigerator, an ice bucket, an adiabatic cooler, and the like.

The one or more prepared vials may be maintained or held at a sub-freezing temperature. For example, the vials may be held at a sub-freezing temperature including about −22° C. The sub-freezing temperature may include temperatures ranging from about −5° C. to about −15° C., about −15° C. to about −20° C., about −15° C. to about −25° C., about −10° C. to about −30° C., about −20° C. to about −40° C., −20° C. to about −50° C., about −20° C. to about −80° C., or less than about −80° C. The vials may be held at a sub-freezing temperature for a period of time sufficiently long in order to allow the mixture in the vials to freeze. For example, the vials may be held at a sub-freezing temperature for about 10 minutes. The vials may be held for about 1 minute to about 5 minutes, from about 5 minutes to about 10 minutes, from about 10 minutes to about 15 minutes, from about 15 minutes to about 20 minutes, from about 20 minutes to about 25 minutes, about 25 minutes to about 30 minutes, about 30 minutes to about 60 minutes, and/or for longer than 60 minutes Embodiment of step S103 of method 100 may include placing the one or more vials onto a pre-cooled shelf of a lyophilizer, for example a VIRTIS™ Benchtop freeze dryer. The pre-cooled shelf of the lyophilizer may be pre-cooled to any suitable temperature. For example, the shelf may be pre-cooled to a temperature that is approximately equivalent to the temperature at which the vials have been maintained during step S103 of method 100. For example, the shelf may be cooled to a temperature of about −20° C. The shelf may be pre-cooled to a temperature of about −15° C. to about −25° C., about −10° C. to about −30° C., about −5° C. to about −35° C., −2° to about −50° C., about −50° C. to about −80° C., about −40° C. to about −90° C., and the like. The pre-cooled shelf may be any suitable shelf of the lyophilizer. The lyophilizer may also be pre-cooled. The one or more vials may be placed in any suitable position on the pre-cooled shelf. For example, the one or more vials may be placed in the center of the shelf, evenly distributed across an upper surface of the shelf, or clustered in a particular location on the shelf as appropriate to ensure proper lyophilization. The one or more vials may be partially capped up to the first groove of the stopper in order to allow for escape of vapor, and then the stopper may be closed under vacuum to allow for the later addition of one or more filling gases, as preferred, and as at least partially described in U.S. Pat. No. 9,700,640 B2.

Embodiments of step S104 of method 100 may include freeze-drying the one or more frozen vials by lyophilizing the vials using any suitable lyophilizing device as understood in the art, for example a VIRTIS™ Benchtop freeze dryer. The one or more vials may be freeze-dried using a lyophilizer for a suitable duration of time so as to assure the desired amount of freeze-drying of the mixture. For example, the vials may be lyophilized for a period including up to about 24 hours. The period may be about 12 hours to about 18 hours, about 18 hours to about 20 hours, about 20 hours to about 24 hours, about 24 hours to about 30 hours, about 30 hours to about 36 hours, and the like. The one or more vials may be freeze-dried at a pressure including below about 300 μbar. For example, the one or more vials may be freeze-dried at a pressure including about 10 μbar to about 100 μbar, about 50 μbar to about 150 μbar, about 100 μbar to about 200 μbar, about 200 μbar to about 300 μbar, and about 250 μbar to about 300 μbar.

Embodiments of step S105 of method 100 may include capping the one or more vials that have been freeze-dried according to step S104. The one or more vials may be capped using any suitable capping mechanism as understood in the art including for example screw caps, snap caps, and the like. The capped vials may then be stored or used, as appropriate.

Annealing

Embodiments of the present invention provide methods 200 for freeze-drying one or more samples of microbubbles using annealing.

Figure 2:
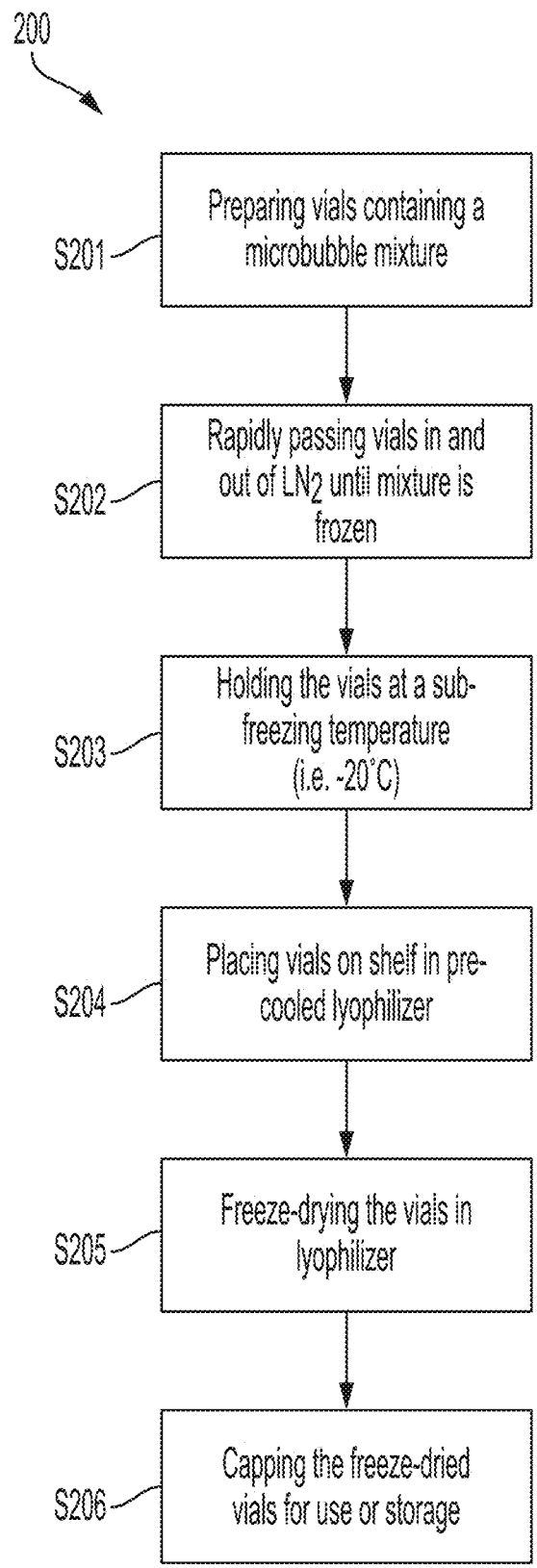
FIG. 2 depicts a schematic of an exemplary annealing freezing method of the present invention.

Referring now to FIG. 2, step S201 of method 200 may include first preparing vials containing a microbubble mixture. The vials may include any suitable vial as understood in the art. For example vials may be constructed from glass, cryoplastic, and the like. The vials may include vials having a volume of up to about 0.5 mL, about 1.0 mL, about 1.5 mL, about 2.0 mL, about 5 mL, and the like. The microbubble mixture may include one or more volumes of microbubbles including surfactant-stabilized microbubbles, as described elsewhere herein. The mixture may further include one or more lyoprotectants, as described elsewhere herein.

Embodiments of step S202 of method 200 may include passing the one or more prepared vials in and out of liquid nitrogen ($LN_2$). Embodiments of step S202 include passing the prepared vials in and out of $LN_2$ rapidly such that the dwell time in $LN_2$ for each iteration lasts no more than about 10 seconds. For example, the dwell time in $LN_2$ for each iteration may be about 0.5 second to about 1 second, about 1 second to about 3 seconds, about 3 seconds to about 5 seconds, about 5 seconds to about 7 seconds, about 7 seconds to about 9 seconds, about 10 or more seconds and the like. The one or more vials may additionally be rocked, swirled or gently agitated during this process, while assuring that the bubbles remain suspended prior to freezing.

The one or more prepared vials may be transferred from a first controlled environment to a second controlled environment. The first controlled environment may have a controlled temperature or room temperature. The first controlled environment may have a controlled temperature including, for example about 20° C., about 20° C. to about 25° C., about 19° C. to about 29° C. and the like. The second controlled environment may be an environment containing $LN_2$. The second controlled environment may be an environment set to a temperature of about −195° C. to about −210° C. The one or more prepared vials may be transferred from the first controlled environment to the second controlled environment using one or more techniques including being physically transferred manually, or using one or more automated techniques or systems, including for example a system (e.g., a robotic system) for automated transfer or displacement of the one or more vials between two environments. In some embodiments, the one or more vials are placed in a device or apparatus that fluctuates between two or more predetermined temperatures. For example, the vials may be placed in a thermocycler or other similar device as understood in the art. The one or more vials may be cycled between the first controlled environment and the second controlled environment for a sufficient duration of time such that the mixture becomes frozen. For example, the one or more vials may be continuously cycled between the two controlled environments (e.g., into and out of the $LN_2$) for about 10 minutes, from about 5 minutes to about 15 minutes, from about 5 minutes to about 20 minutes, from about 5 minutes to about 25 minutes, from about 5 minutes to about 30 minutes, and the like. During each cycle of transferring between the first and second controlled environment, the one or more vials may be positioned in the cooled second controlled environment (e.g., $LN_2$) for about 5 seconds, about 2 seconds to about 10 seconds, about 2 seconds to about 20 seconds, and the like. In some embodiments, the one or more vials are transferred manually. In some embodiments, the vials are positioned in a device including for example a thermocycler such that the vials are stationary and the device transitions between a first controlled temperature (e.g., room temperature) and a second controlled temperature (e.g., from about −195° C. to about −210° C.).

Embodiments of step S203 of method 200 may include holding or maintaining the vials at a sub-freezing temperature. For example, the vials may be held at about −20° C. The vials may be held at a sub-freezing temperature that may include temperatures ranging from about −5° C. to about −15° C., about −15° C. to about −20° C., about −20° C. to about −30° C., and/or about −30° C. to about −40° C. The vials may be held at a sub-freezing temperature overnight. For example, the vials may be held at a sub-freezing temperature for up to about 12 hours, about 12 hours to about 18 hours, about 18 hours to about 24 hours, and the like.

Embodiments of step S204 of method 200 may include placing the frozen vials on a pre-cooled shelf of a lyophilizer. The pre-cooled shelf of the lyophilizer may be pre-cooled to any suitable temperature. For example, the shelf may be pre-cooled to a temperature that is approximately equivalent to the temperature that the vials have been incubated in during step S203 of method 200. For example, the shelf may be cooled to a temperature of about −20° C. The shelf may be pre-cooled to a temperature of about −15° C. to about −25° C., about −10° C. to about −30° C., about −5° C. to about −35° C., and/or about −2° to about −50° C. The pre-cooled shelf may be any suitable shelf of the lyophilizer. The lyophilizer may also be pre-cooled. The one or more vials may be placed in any suitable position on the pre-cooled shelf. For example the one or more vials may be placed in the center of the shelf, evenly distributed across an upper surface of the shelf, or clustered in a particular location on the shelf as appropriate to ensure proper lyophilization.

Embodiments of step S205 of method 200 may include freeze-drying the one or more frozen vials by lyophilizing the vials using any suitable lyophilizing device as understood in the art. The one or more vials may be freeze-dried using a lyophilizer for a suitable duration of time so as to assure the desired amount of freeze-drying of the mixture. For example, the vials may be lyophilized for a period including up to about 24 hours. The period may be about 12 hours to about 18 hours, about 18 hours to about 20 hours, about 20 hours to about 24 hours, about 24 hours to about 30 hours, about 30 hours to about 36 hours, and the like.

Embodiments of step S206 of method 200 may include capping the one or more vials that have been freeze-dried according to step S205. The one or more vials may be capped using any suitable capping mechanism as understood in the art including, for example, using screw caps, snap caps, and the like. The one or more vials may be capped under vacuum. The capped vials may then be stored or used, as appropriate.

Kits

The invention further provides kits including the elements disclosed elsewhere herein. A set of instructional materials can also be provided in the kit. The instructional materials can contain written, pictorial, and/or video directions on using the materials of the kit, including the methods of the invention.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Figure 3:
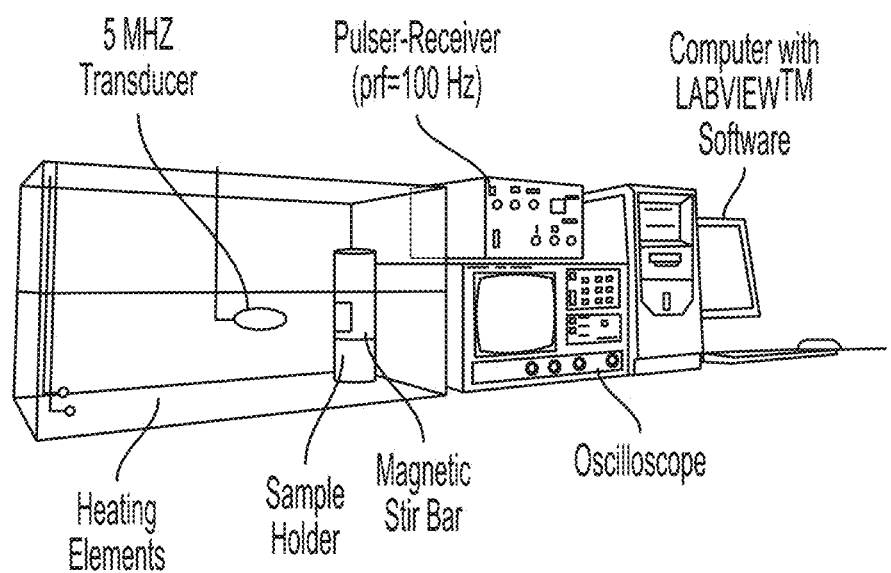
FIG. 3 depicts an exemplary acoustic testing setup used to generate dose response curves of acoustic enhancement with increased contrast agent dose and to generate time-response curves of loss of acoustic enhancement under constant insonation.

Example 1: Evaluation of Efficacy of Microbubbles Following Freeze Drying Using Different Methods Introduction In order to evaluate the efficacy of various methods for freeze drying microbubbles used as ultrasound contrast agents, surfactant-stabilized microbubbles (i.e. SE61, composed of sorbitan monostrearate (e.g., SPAN® 60) and water-soluble vitamin E (d-alpha-Tocopheryl polyethylene glycol 1000 succinate (TPGS)) were freeze-dried using various methods and evaluated for their echogenicity. Freezing profiles were obtained using thermocouples inserted into lyophilization vials containing microbubble samples. Acoustic testing was performed in an in vitro setup such as that described in FIG. 3.

Methods and Results

Figures 4A, 4B:
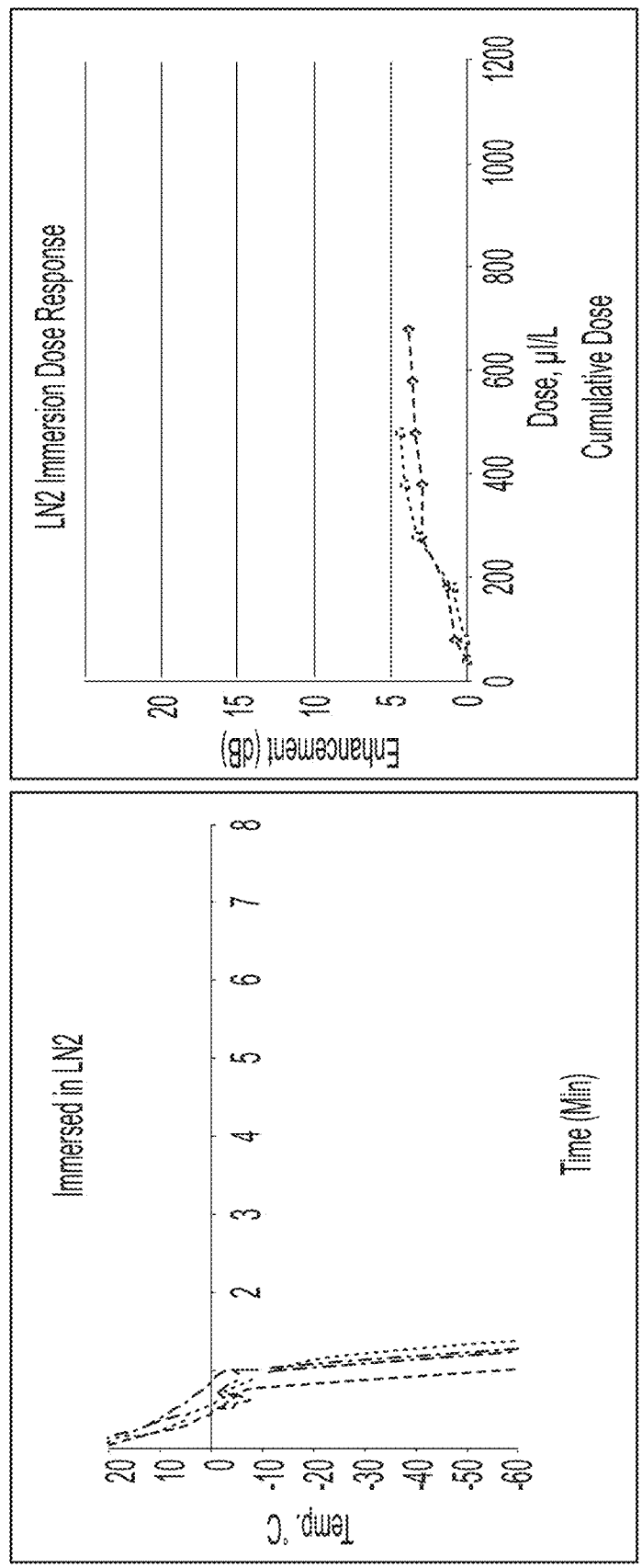
FIGS. 4A and 4B depict data curves illustrating the effects of plunging samples into liquid nitrogen ($LN_2$).

Flash freezing by immersing contrast agent contained in a glass vial into liquid nitrogen ($LN_2$), and freeze drying without holding at −80° C. is a standard method for freezing compound. However, this method has been shown to not produce echogenic bubbles (shown in FIGS. 4A and 4B). Rapid freezing can prevent the formation of large ice crystals, but melt back was observed after drying. Another approach that was taken involved holding at a set temperature (annealing), which allows the growth of larger crystals. This was likely what was taking place during the hold period with the refrigerant ST68. For SE61-based contrast agents, this method did not work.

Figures 5A, 5B:
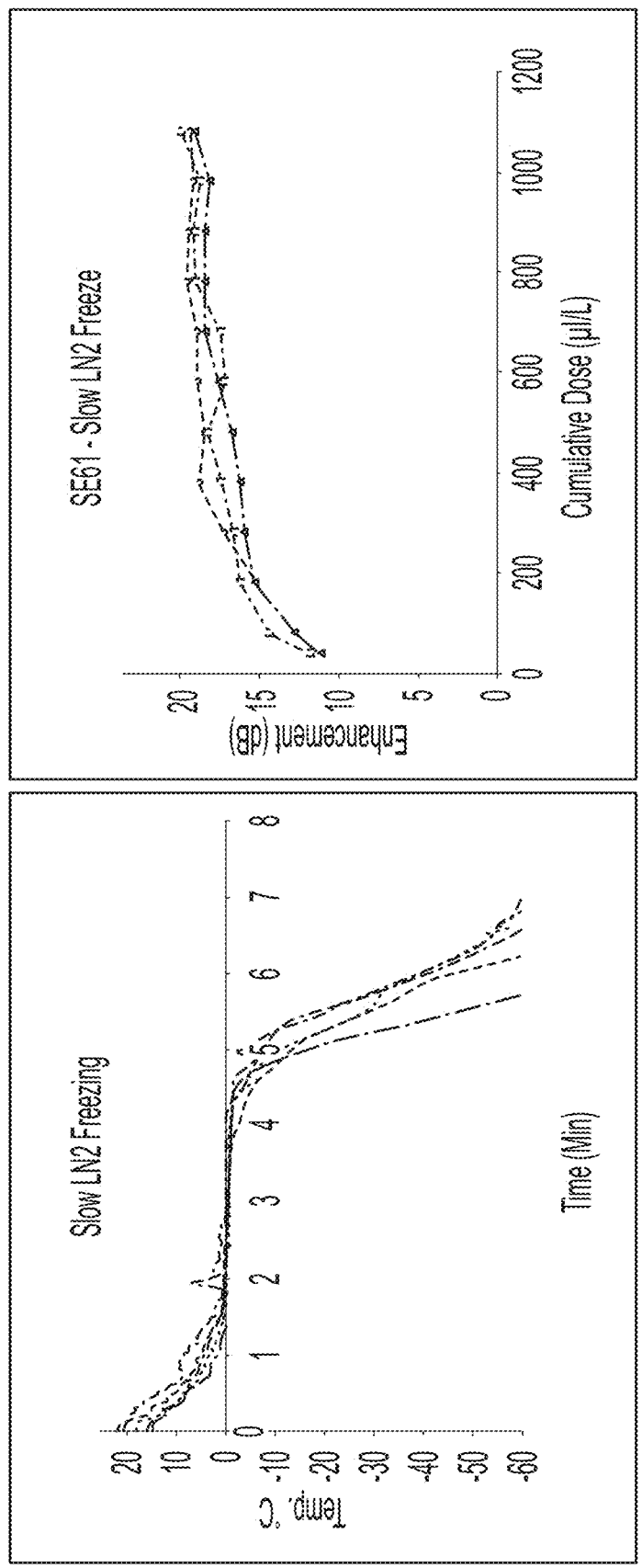
FIGS. 5A and 5B depict data curves illustrating the effects of freezing with small aliquots of $LN_2$ poured over vials of contrast agent samples.

One method that was found to be successful was freezing vials of contrast agents with small aliquots of $LN_2$ poured over the vials. This approach slowed down the rate of freezing, shown by the prolonged time (2-3 minutes) at 0° C. (shown in FIGS. 5A and 5B). This prolonged freezing time allows for the growth of ice crystals. Contrast agent prepared with this freezing method had good maximum enhancement of around 20 dB (shown in FIGS. 5A and 5B). However, since this method involved manually pouring small amounts of $LN_2$, this method was also operator-dependent, and very cumbersome.

One consideration for freeze drying in a manner that retains echogenicity is that the temperature needs to be cold enough to freeze the mixture quickly before the bubbles rise out of solution, but slow enough to allow crystallization for drying. The temperature of −20° C. was chosen and tested. However, temperatures colder than −20° C. may also show efficacy.

Figures 6A, 6B:
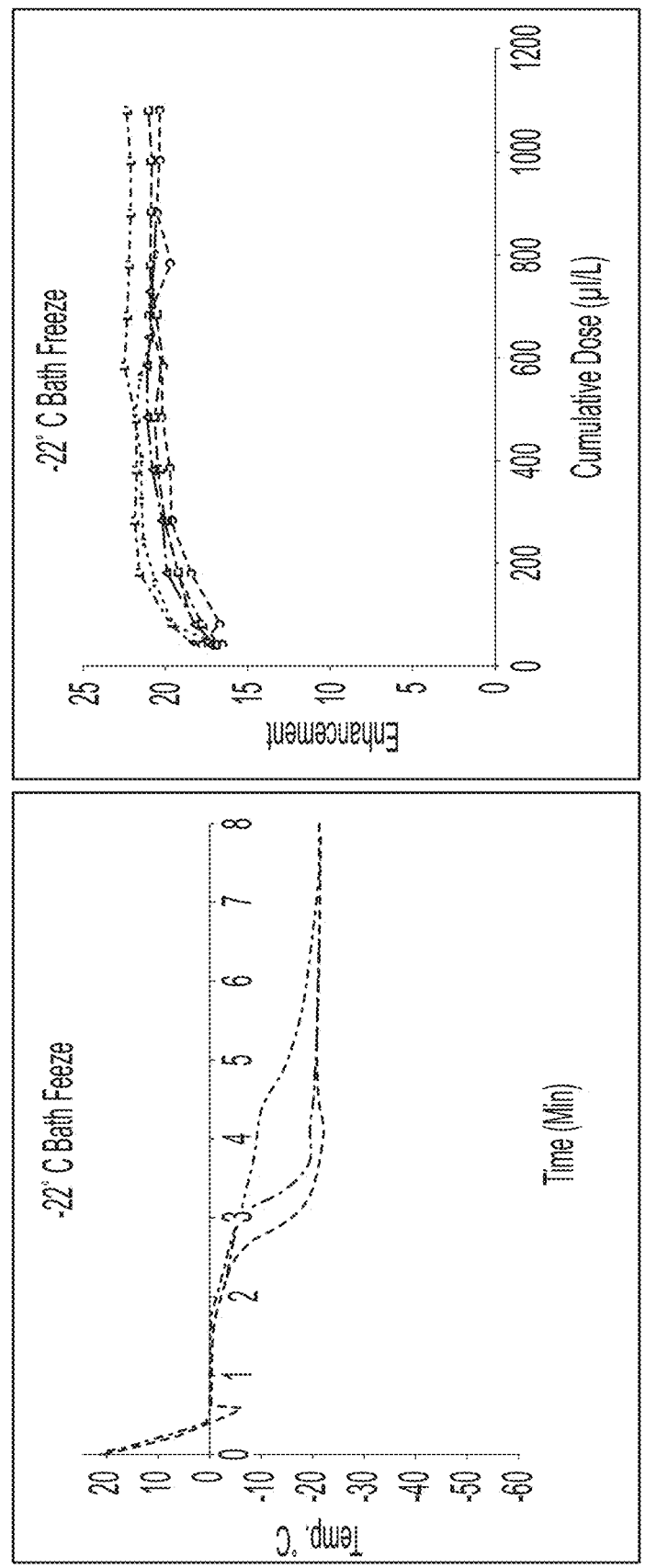
FIGS. 6A and 6B depicts data curves illustrating the effects of freezing samples using a chilled water bath maintained at a temperature near $-22°$ C.

Vials containing contrast agent and lyoprotectant were partially submerged in a chilled water bath near −22° C. and held there for about 10 minutes until frozen. The vials were then placed on the cooled (−20° C.) shelf of the lyophilizer. The vials were then freeze-dried and capped similarly to other methods. This new method produces a similar freezing pattern as using the slow $LN_2$ freezing method described above, and results in contrast agent samples with similar maximum enhancement of around 20 dB (shown in FIGS. 6A and 6B), but is not operator-dependent or cumbersome. This method allows for a more controlled freezing profile, ensuring that proper crystallization of the contrast agent solution occurs in a more repeatable and standardized manner.

Example 2: Preserving the Integrity of Surfactant-Stabilized Microbubble Membranes for Localized Oxygen Delivery Introduction Ultrasound contrast agents have evolved dramatically since researchers first identified that the shadowing on an ultrasound scan upon injection of indocyanine green was from a swarm of tiny bubbles generated at the needle tip (Nanda, N. C., History of echocardiographic contrast agents. Clin. Cardiol. 1997, 20 (51), 7-11). Stabilized microbubbles now span a wide spectrum of chemical compositions and potential clinical applications, from conventional ultrasound imaging and nonlinear imaging, through targeting and molecular imaging to multimodal imaging and drug and gene delivery (Chong, W. K.; Papadopoulou, V.; Dayton, P. A., Imaging with ultrasound contrast agents: current status and future. Abdom. Radiol. 2018, 43 (4), 762-772; Li, Y.; Chen, Y.; Du, M.; Chen, Z.-Y., Ultrasound technology for molecular imaging: from contrast agents to multimodal imaging. ACS Biomat. Sci. Eng. 2018, 4 (8), 2716-2728). By virtue of the large differences in the acoustical impedance between the gas within these agents and the surrounding fluid (blood), a substantial acoustic backscatter is created which increases the overall contrast of the ultrasound image (Hoff, L., Acoustic properties of ultrasonic contrast agents. Ultrasonics 1996, 34 (2-5), 591-593). For intravenous injection, the agents must be less than 6 µm in diameter to transit the pulmonary bed, and possess a stabilizing shell, usually phospholipid, polymer or surfactant.

While the majority of reports involve phospholipid shells, others have included such compounds as poloxamer, PEG-40-stearate, and polyvinyl alcohol, used singly and in combination with lysozyme (Ando, Y.; Tabata, H.; Sanchez, M. l.; Cagna, A.; Koyama, D.; Krafft, M. P., Microbubbles with a self-assembled poloxamer shell and a fluorocarbon inner gas. Langmuir 2016, 32 (47), 12461-12467; Cavalieri, F.; El Hamassi, A.; Chiessi, E.; Paradossi, G., Stable polymeric microballoons as multifunctional device for biomedical uses: synthesis and characterization. Langmuir 2005, 21 (19), 8758-8764; Mahalingam, S.; Raimi-Abraham, B. T.; Craig, D. Q.; Edirisinghe, M., Formation of protein and protein-gold nanoparticle stabilized microbubbles by pressurized gyration. Langmuir 2014, 31 (2), 659-666; Owen, J.; Kamila, S.; Shrivastava, S.; Carugo, D.; Bernadino de la Serna, J.; Mannaris, C.; Pereno, V.; Browning, R.; Beguin, E.; McHale, A. P., The Role of PEG-40-stearate in the Production, Morphology, and Stability of Microbubbles. Langmuir 2018). Surfactant-stabilized microbubbles that are formed by sonication of a dual surfactant solution that is saturated with a perfluorocarbon (PFC) gas have been investigated. The mixed surfactants self-assemble around hydrophobic gas bubbles forced out of solution by cavitation.

Figure 16:
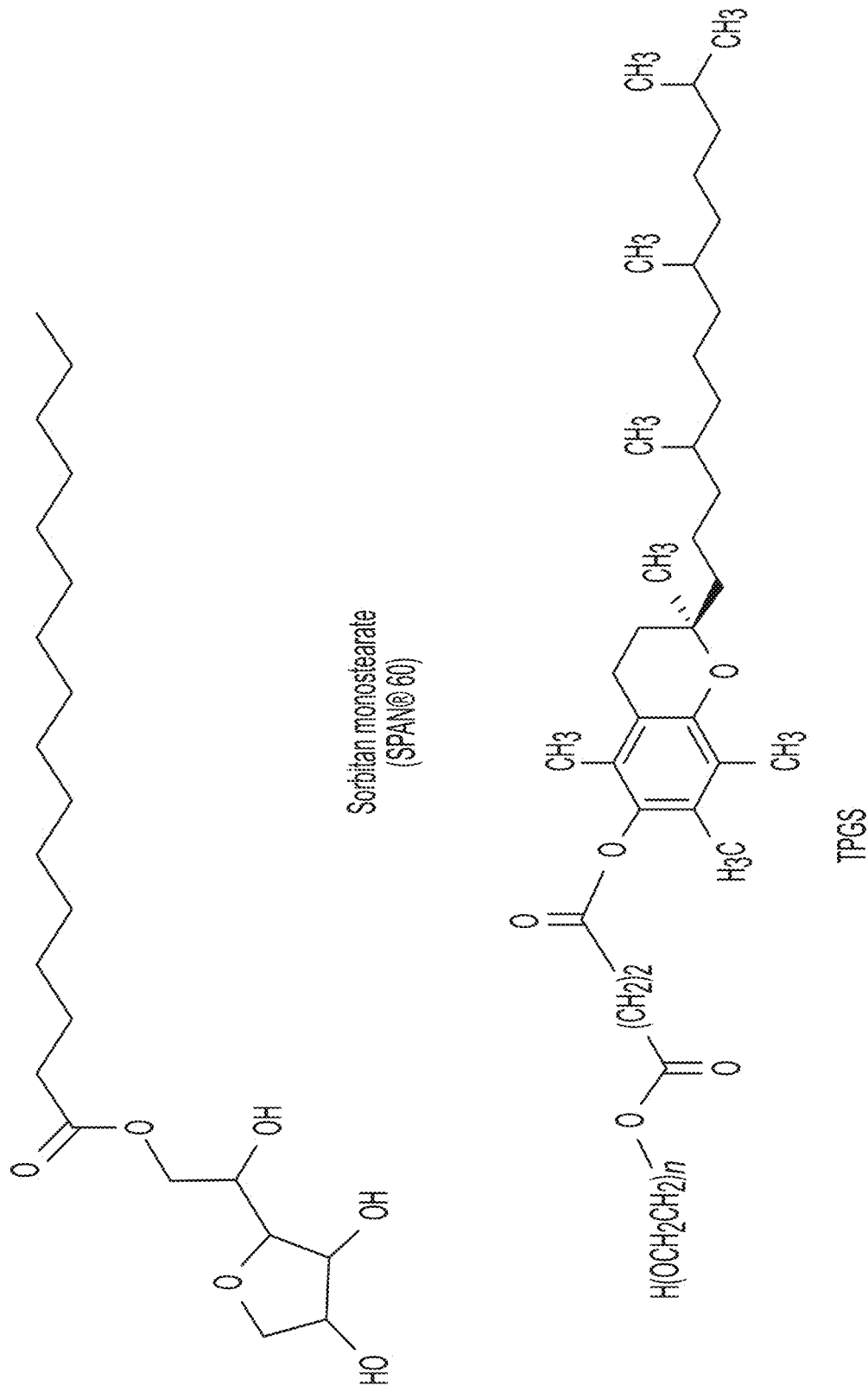
FIG. 16 depicts an exemplary sorbitan monostearate (SPAN® 60) molecule and an exemplary TPGS molecule, the constituents of SE61 as described herein.

A surfactant-stabilized microbubble platform with a shell composed of sorbitan monostearate (e.g., SPAN® 60) and water-soluble vitamin E (α-tocopheryl polyethylene glycol succinate, abbreviated as TPGS), which has been named SE61 has been developed, illustrated in FIG. 16, and is described herein. This is a second generation agent in which the highly versatile TPGS (Tan, S.; Zou, C.; Zhang, W.; Yin, M.; Gao, X.; Tang, Q., Recent developments in d-α-tocopheryl polyethylene glycol-succinate-based nanomedicine for cancer therapy. Drug Del. 2017, 24 (1), 1831-1842) has been employed to replace the less biocompatible TWEEN® 80 (Polysorbate 80) used in the initial agent, ST68. The SE61 microbubbles are first generated in phosphate buffered saline (PBS) purged with PFC gas (labeled $SE61_{PFC}$) because the highly hydrophobic and dense gas produces the highest yields. Freeze-drying these bubbles gives the added advantage that they can be charged with a gas of choice, even one that would have produced a much diminished yield compared with the PFC. These microbubbles have been successfully investigated for oxygen delivery to hypoxic tumors (Eisenbrey, J. R.; Albala, L.; Kramer, M. R.; Daroshefski, N.; Brown, D.; Liu, J.-B.; Stanczak, M.; O'Kane, P.; Forsberg, F.; Wheatley, M. A., Development of an ultrasound sensitive oxygen carrier for oxygen delivery to hypoxic tissue. Int. J. Pharm. 2015, 478 (1), 361-367; Eisenbrey, J. R.; Shraim, R.; Liu, J.-B.; Li, J.; Stanczak, M.; Oeffinger, B.; Leeper, D. B.; Keith, S. W.; Jablonowski, L. J.; Forsberg, F., Sensitization of Hypoxic Tumors to Radiation Therapy Using Ultrasound-Sensitive Oxygen Microbubbles. Int. J. Rad. Oncol. Biol. Physics 2018, 101 (1), 88-96).

The ability of sugars to stabilize dried liposomes, which share similarities to surfactant stabilized microbubbles, have been extensively studied. Dehydration of phospholipids increases the liquid crystalline to gel melt transition temperature (Tm), so that at temperatures normally resulting in the liquid crystalline phase are instead in the gel phase, and subsequently during rehydration, unprotected samples go through a transition back to the liquid crystalline phase, causing liposome disruption (Crowe, L. M.; Crowe, J. H.; Rudolph, A.; Womersley, C.; Appel, L., Preservation of freeze-dried liposomes by trehalose. Arch. Biochem. Biophys. 1985, 242 (1), 240-247). The addition of sugars in larger amounts can prevent this increase of Tm during drying and thus prevent liposome disruption during rehydration. This ability of sugars to reduce the phase transition temperature of phospholipids has been shown to be largely due to the osmotic and volumetric properties of the sugars, including glucose and sorbitol (Koster, K. L.; Webb, M. S.; Bryant, G.; Lynch, D. V., Interactions between soluble sugars and POPC (1-palmitoyl-2-oleoylphosphatidylcholine) during dehydration: vitrification of sugars alters the phase behavior of the phospholipid. BBA-Biomembranes 1994, 1193 (1), 143-150; van Winden, E. C.; Crommelin, D. J., Short term stability of freeze-dried, lyoprotected liposomes. J. Control Rel. 1999, 58 (1), 69-86). It has also been suggested that molecules positioned at the sugar-bilayer interface may behave differently than those in the glassy matrix by creating a mixed phase or accumulating water molecules.

The motivation for this study was that upon moving from the original ST68PFC platform to $SE61_{O2}$, Applicants experienced inconstant results and loss of activity after one week stored as a lyophilized powder at room temperature following the previously determined methods for freeze-drying developed for ST68PFC. One advantage of dealing with ultrasound contrast agent is that the effects that various manipulations have on the integrity of the microbubbles can be monitored by conducting in vitro acoustic testing on the rehydrated samples, because reflection of the ultrasound requires the membrane of the microbubble to be intact. As consistent acoustic readings prior to freeze-drying yielded expected results, freeze-drying was identified as the critical step. Specifically, it was observed that slowing the rate of freezing of the microbubble solution by limiting the exposure to liquid nitrogen produced more intact microbubbles as indicated by better enhancement. Therefore, this new rate of freezing was quantified, a method was determined to reliably reproduce it and the acoustical and physical properties of $SE61_{O2}$ created with this new process measured.

Applicants also observed a loss of initial ultrasound enhancement during room temperature storage of freeze-dried samples that exhibited acceptable initial acoustical properties. Shelf-life stability has not previously been tested for $SE61_{O2}$, but has been reported as stable over several months for ST68PFC. In an initial investigation of 5.0% (w/v) solutions, glucose remained the lyoprotectant of choice, outperforming trehalose, polyvinylpyrrolidone, and polyvinyl alcohol. Therefore, the shelf-life of $SE61_{O2}$ and the effect of increasing the concentration of glucose lyoprotectant was investigated. To investigate the stability of microbubble membranes at the interface during freeze-drying, different techniques were employed including monitoring freezing and drying temperature profiles, differential scanning calorimetry (DSC) to determine the phase transitions during freezing and in dried samples, and the acoustic response of the gas filled and rehydrated agent with size and bubble counts to determine damage to the microbubble shell integrity.

Materials and Methods

Materials

SPAN® 60 was obtained from Sigma Aldrich, (St. Louis, Mo.) and TPGS from Eastman Chemical Company, Kingsport, Tenn.). D-(+)-glucose anhydrous was obtained from Fluka BioChemica (Switzerland). Octafluoropropane (PFC) from Advanced Specialty Gasses, (Reno, Nev.), and oxygen from Airgas (Radnor, Pa.) were passed through a 0.2 μm sterile filter before use. Countbright™ absolute counting beads (Life Technologies, Grand Island, N.Y., 0.54×105 beads/50 μl) were used as a reference standard for the flow cytometer experiments. All other chemicals were analytical grade from Sigma Aldrich (St. Louis, Mo.), and used as received.

Microbubble Fabrication

Microbubble mixtures were fabricated based on a previously reported method, then freeze-dried (Eisenbrey, J. R.; Albala, L.; Kramer, M. R.; Daroshefski, N.; Brown, D.; Liu, J.-B.; Stanczak, M.; O'Kane, P.; Forsberg, F.; Wheatley, M. A., Development of an ultrasound sensitive oxygen carrier for oxygen delivery to hypoxic tissue. Int. J. Pharm. 2015, 478 (1), 361-367). Briefly, surfactant mixtures of TPGS and sodium chloride in PBS were autoclaved, then allowed to cool to room temperature under continuous stirring in order to form an intimate mixture and decrease the solid particle size. The cooled mixture was placed in a beaker in an ice bath and continuously sonicated at 20 kHz for 3 min at 110 W using a 0.5-inch probe horn (Misonix Inc., Farmingdale, N.Y.). The solution was purged with a steady stream of PFC gas before and during the sonication.

Microbubbles were separated from the mixture via gravity separation in a 250 mL glass separation funnel. While in the funnel, the solution forms three layers. The mixture was washed 3 times with cold (4° C.) PBS, with a 90 minute separation after the first 2 washes and a 60 minute separation after the final wash. During this separation time, the microbubbles collect in a middle band in the funnel, and after each wash the bottom layer was discarded. After the third wash and separation, the middle microbubble fraction was collected after discarding the bottom layer. The collected microbubbles were then diluted 1:1 by volume with one of three lyoprotectant solutions resulting in the following concentrations: 1.8% (w/v) glucose-PBS solution, 1.8% (w/v) glucose-water solution, and a 5.0% (w/v) glucose-water solution. Once mixed, 4 mL aliquots of $SE61_{PFC}$ solution were pipetted into 20 mL lyophilization vials obtained from West Pharmaceutical Services (Lionville, Pa.). Samples were frozen either by exposure to liquid nitrogen or by being placed into a recirculating chiller bath (Haake D1 and G, Germany) containing equal parts water and propylene glycol chilled to −20° C. Once samples were frozen, lyophilization stoppers were placed on the vials to the first grove, the vials placed onto a previously chilled (−20° C.) shelf, and were dried for 18-20 hours using a VIRTIS Benchtop freeze-dryer (Gardiner, N.Y.) at pressures below 300 μbar and a condenser temperature less than −70° C. At the end of the cycle, prior to venting, a piston was lowered to seal the stoppers on the vials under vacuum.

Temperature Profiles

To measure the temperature profile of samples during freezing and drying, type T thermocouples were placed in the vial, roughly at the center of the $SE61_{PFC}$ solution and the temperature was recorded using an Omega (Norwalk, Conn.) HH147U data logger thermometer, every second during freezing and once every 30 s during drying.

Sample Preparation

Prior to acoustical testing, lyophilized samples were filled with oxygen, introduced via a needle through the stopper. Freeze-dried $SE61_{O2}$ was then reconstituted by hand agitation with either 4 mL of DI water (glucose-PBS samples) or with 2 mL each of DI water and PBS (glucose-water samples) to create samples with identical salinity. All samples were stored at room temperature, approximately 22° C. until use.

Bubble Counting

Particle counting was performed using a flow cytometer, LSRII (BD Biosciences, San Jose, Calif.) at room temperature. Samples were prepared by adding 20 μl of reconstituted microbubbles to 0.5 ml of deionized water and 20 μl of UV COUNTBRIGHT™ absolute counting beads (containing 10,800 beads as a counting standard). Flow data were analyzed using FLOWJO® software (Tree Star, Inc. Ashland, Oreg., USA). Counting beads and SE61 microbubbles were first separated using forward scattering (FSC-A) and florescence (FITC-A gate), then the remaining microbubbles were plotted using FSC-A vs side scattering (SSC-A) to observe changes in bubble populations, and divided into four areas of interests, based on count density to obtain bubble counts. These quadrants were kept constant for all samples.

Microbubble Size Measurement

The sizes of microbubbles were determined by dynamic light scattering measured using a ZETASIZER® Nano ZS (Malvern Inst., Worcestershire, UK). Samples of 50 μl were dispersed in 950 μl PBS. Samples were measured at 25° C. using a backscattering angle of 173°, and the automatic measurement detection option was selected, resulting in a typical run time of 60 seconds. Samples were measured in triplicate and particle sizes were reported as Z averages based on the resultant intensity readings.

Acoustic Characterization

To monitor acoustic behavior in vitro we utilized a custom-built acoustic setup, which closely mimics in vivo conditions (Wheatley, M. A.; Forsberg, F.; Oum, K.; Ro, R.; El-Sherif, D., Comparison of in vitro and in vivo acoustic response of a novel 50:50 PLGA contrast agent. Ultrasonics 2006, 44 (4), 360-367). Briefly, the setup consists of a pulsed A-mode ultrasound system fitted with an OLYMPUS® (Waltham, Mass.) 5 MHz transducer with a 12.7 mm diameter and focal length of 49.3 mm. Acoustic pressure amplitudes were generated using a PANAMETRICS® pulser/receiver setup (model 5072 PR) using a pulse repetition frequency (PRF) of 100 Hz generating peak positive and negative pressures of 0.69 and 0.45 MPa respectively. Received signals were amplified 40 dB and read using a digital oscilloscope (LECROY® 9350A, LeCroy Corp., Chestnut Ridge, NY), and the data processed using LABVIEW® software (National Instruments, Austin, Tex.). The transducer was focused through an acoustic window of a custom-made sample vessels submerged in a deionized water bath (37° C.), with the contents continuously stirred during testing. Cumulated dose response curves, signal returned to the transduced as a function of microbubble dose, were constructed by pipetting increments of $SE61_{O2}$ into the sample chamber containing 50 mL of PBS at 37° C. while measuring the acoustic response. To examine the stability of $SE61_{O2}$ while being exposed continuously to an ultrasound beam, a dose on the rise of the dose response curve, in this case 180 μl/L, was insonated over a 10 min period using the same acoustic parameters used for the dose response studies. Readings were taken every minute, starting at t=0 (time immediately post injection), for a total of 11 readings, with data normalized by the initial dB value to allow for comparison.

Thermal Properties

DSC scans of $SE61_{PFC}$ solutions and dried product were conducted using a T.A. INSTRUMENTS Q2000 (New Castle, Del.) differential scanning calorimeter. All samples started at 25° C., and were heated and cooled at a rate of 10° C./min. For SE61 solutions, samples were cooled to −90° C., then heated to 15° C. using a 20 μl sample. Dried SE61 samples were cooled to −20° C. then heated to 80° C. using approximately a 3 mg sample.

Statistical Analysis

All data are presented as standard deviation about the mean. Acoustical data were measured from three microbubble lots, with each repeated 3 times (n=3). Bubble counts and size data were obtained from one lot with each repeated 3 times (n=1). Statistical significances between days for the acoustical stability study was determined via a multi-factorial repeated measures ANOVA, while differences between size and bubble concentrations were determined using ANOVA and a Bonferroni post hoc (as needed), both using SPSS 25 (IBM, Armonk, N.Y.).

Results

Determination of Freezing Method

Figure 7:
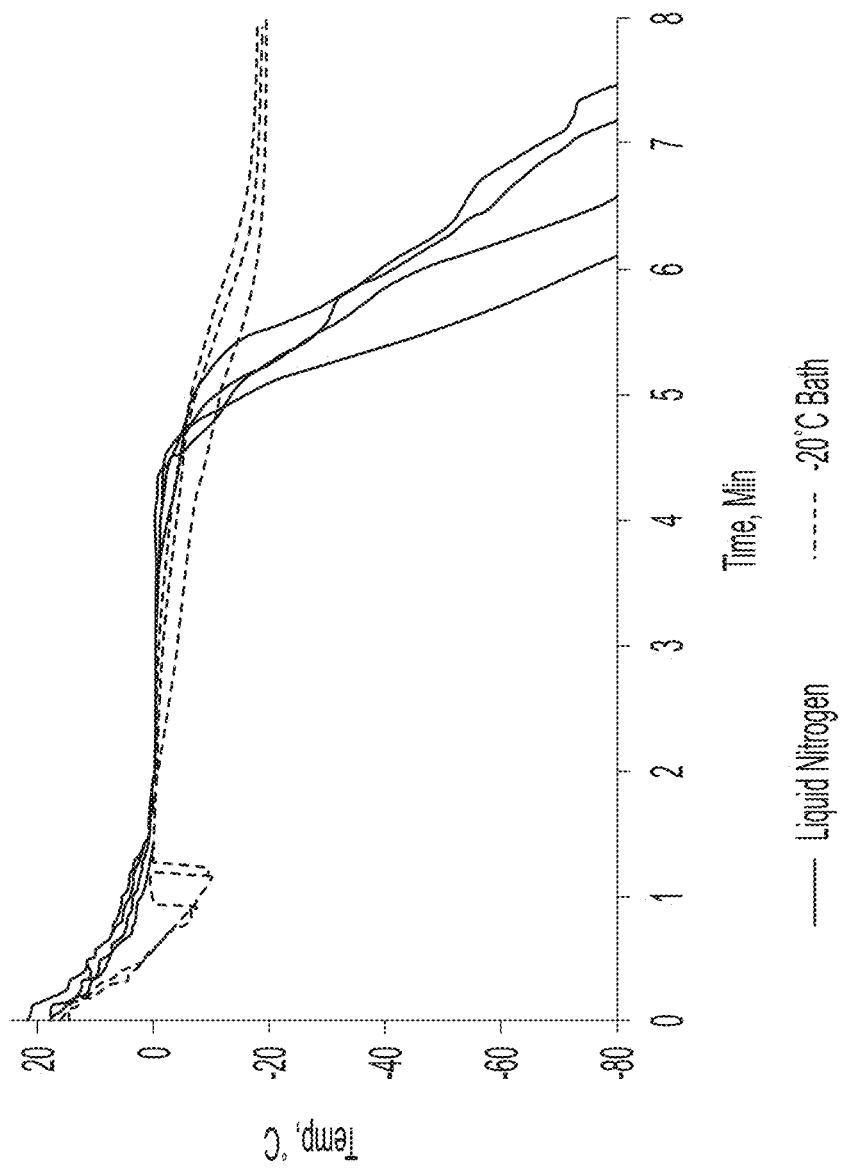
FIG. 7 depicts typical temperature profiles of $SE61_{PFC}$ during freezing. The solid and dotted lines illustrate a comparison of use of liquid nitrogen or a $-20°$ C. bath.

In previous in vivo studies, a method of freezing SE61 (1.8% (w/v) Glucose in PBS) with liquid nitrogen was developed, in which liquid nitrogen was slowly poured over agitated vials to gradually reduce the temperature. Measured temperature profiles of this method that produced viable, echogenic microbubbles with a response higher than 15 dB, which has been determined to be required for in vivo effectiveness (Wheatley, M. A.; Forsberg, F.; Oum, K.; Ro, R.; El-Sherif, D., Comparison of in vitro and in vivo acoustic response of a novel 50:50 PLGA contrast agent. Ultrasonics 2006, 44 (4), 360-367) can be found in the solid lines in FIG. 7, and show that the microbubble solution was brought to 0° C. over a period of around 1.5 minutes. The solution then remained at 0° C. for approximately 3 minutes as ice crystallization occurred, and then was cooled rapidly by longer exposure to the liquid nitrogen. However, the exact freezing profile, and resulting acoustic properties, showed inter-batch variability. This was attributed to the high operator-dependency of the pouring method. It was found that the successful freezing profile could be approximated reproducibly by utilizing a −20° C. chilled bath in which the vials were placed with mechanical agitation to keep the microbubbles suspended until frozen. The temperature profiles for samples frozen in the chilled bath, also in FIG. 7, show a somewhat more rapid cooling followed by supercooling of the liquid before ice crystallization occurred after about 1 minute. Mirroring the slow liquid nitrogen method, the microbubble solution remained at near 0° C. for approximately 2-3 minutes during ice crystallization, then slowly cooled to the bath temperature. After freezing by either method, the frozen samples were rapidly transferred to the stage of the freeze drier which had been cooled to −20° C., and lyophilization was initiated.

Acoustical Characterization

Figure 8:
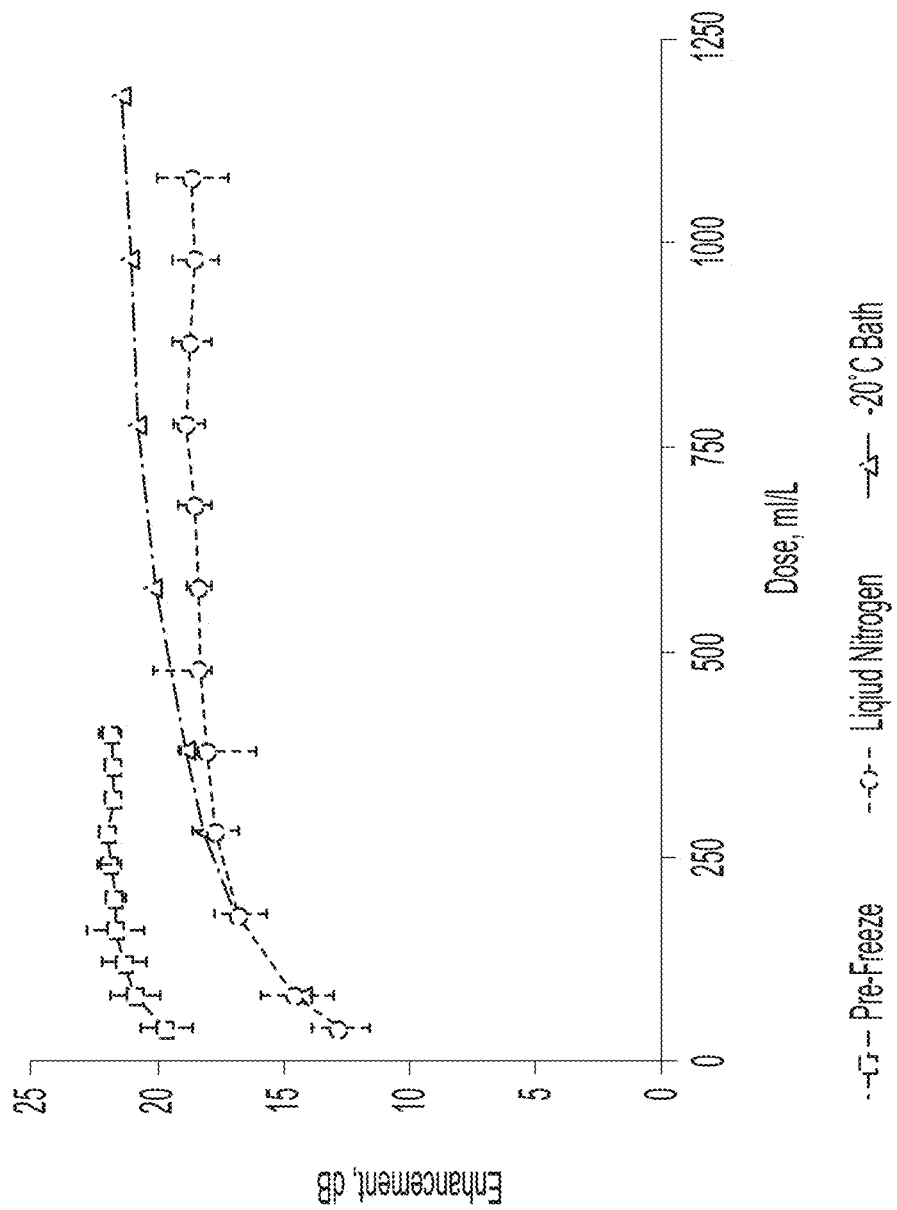
FIG. 8 depicts dose response curves of pre-freeze-dried $SE61_{PFC}$ and reconstituted $SE61_{O2}$ as a function of freezing method.

Dose response curves were conducted on $SE61_{PFC}$ samples prior to freezing (after diluting 1:1 with lyoprotectant), and $SE61_{O2}$ prepared with both freezing methods, charged with oxygen and resuspended in water to give a final salt concentration equivalent to PBS. Recording of the $SE61_{PFC}$ echogenicity was continued until the profile was established. As FIG. 8 shows, while freeze-drying results in a higher dose needed to achieve a similar echogenicity to the pre-freeze-dried samples which have a value of 21.6±0.4 dB at a smaller dose of 200 µl/L, both freezing methods produce $SE61_{O2}$ with reproducible and equivalent enhancement to that previously reported (Solis, C.; Forsberg, F.; Wheatley, M. A., Preserving enhancement in freeze-dried contrast agent ST68: Examination of excipients. Int. J. Pharm 2010, 396 (1-2), 30-38). At a dose of 580 µl/L, the slow liquid nitrogen freeze and −20° C. bath samples have an enhancement of 18.3±0.5 and 20.2±0.3 dB respectively. Although statistically different (p<0.01), both of these enhancements are greater than the 15 dB required for in vivo effectiveness (Wheatley, M. A.; Forsberg, F.; Oum, K.; Ro, R.; El-Sherif, D., Comparison of in vitro and in vivo acoustic response of a novel 50:50 PLGA contrast agent. Ultrasonics 2006, 44 (4), 360-367), therefore both methods were determined to produce suitable microbubbles. Freezing for the rest of the study was conducted using the −20° C. bath based on ease of use and the potential to reduced operator variability. Without being bound to theory, it is hypothesized that both methods, with reduced freezing rates compared to the previous method of immersing in liquid nitrogen, allowed the glucose to become more concentrated around the microbubbles, providing better protection during drying, as has been shown in the case of freeze-drying nanoparticles (Lee, M. K.; Kim, M. Y.; Kim, S.; Lee, J., Cryoprotectants for freeze-drying of drug nano-suspensions: effect of freezing rate. J. Pharm. Sci. 2009, 98 (12), 4808-4817). The small improvement of using the −20° C. bath over the slow liquid nitrogen freeze is therefore a result of more control of the freezing profile resulting in lower inter-lot variability. While the freeze-dried samples had a reduced enhancement and required a higher dose to achieve their maximum, these altered acoustical curves are in agreement with those reported with freeze-dried ST68.

TABLE 1

|  |  | Size | Flow Cytometery | | |
|---|---|---|---|---|---|
|  |  | Z Average (µm) | Total Microbubbles/mL | Microbubbles Q1 | Microbubbles Q4 |
| Pre-Dried $SE61_{PFC}$ 1.8% (w/v) glucose-PBS | Day 0 | 1.16 ± 0.20 | 67.6 ± 4.3E+07 | 29.6 ± 0.5E+07 | 35.7 ± 3.5E+07 |
| $SE61_{O2}$ - 1.8% (w/v) glucose-PBS | Day 0 Day 7 Change | 2.55 ± 0.53 1.79 ± 0.23 −29.7% | 17.8 ± 1.2E+07 9.6 ± 0.4E+07 −45.9% | 3.6 ± 0.1E+07 1.0 ± 0.0E+07 −72.8% | 12.5 ± 1.2E+07 7.5 ± 0.3E+07 −40.2% |
| $SE61_{O2}$ - 1.8% (w/v) glucose-water | Day 0 Day 7 Change | 2.17 ± 0.40 1.39 ± 0.26 −36.1% | 22.8 ± 1.9E+07 15.2 ± 0.9E+07 −33.4% | 6.0 ± 1.1E+07 1.9 ± 0.1E+07 −67.8% | 14.6 ± 0.9E+07 11.4 ± 0.7E+07 −21.6% |
| $SE61_{O2}$ - 5.0% (w/v) glucose-water | Day 0 Day 7 Change | 1.47 ± 0.22 1.42 ± 0.16 −3.3% | 15.3 ± 2.4E+07 11.8 ± 0.7E+07 −22.5% | 3.1 ± 0.9E+07 2.6 ± 0.4E+07 −18.0% | 11.1 ± 1.3E+07 8.1 ± 0.3E+07 −26.9% |

For a given bubble composition, acoustic enhancement is a function of bubble sizes and concentrations and these are summarized in Table 1. Pre-freeze $SE61_{PFC}$ bubbles were found to have an average size of 1.16±0.2 µm and a concentration of 67.6±4.3 E+07 bubbles/mL, while freeze-dried $SE61_{O2}$ bubbles increased to 2.55±0.4 µm (p<0.01) with a decreased concentration of 17.8±1.2 E+07 bubbles/mL (p<0.01). The observed shift in the acoustical dose curve is a result of this decrease in bubble concentration. While bubbles are likely lost during drying, part of this decrease can be explained by the amount of solution used to reconstitute the freeze-dried bubbles. Historically, the amount of reconstitution fluid has equaled the amount of lyoprotectant and contrast bubbles (4 mL) added to the vials prior to freeze-drying. However, as half of that initial solution is microbubbles, which consist mainly of gas and not liquid, it follows that the freeze-dried samples are being reconstituted in a larger volume of liquid, potentially diluting the concentration.

Thermal Properties of SE61 Solutions

Figure 9B:
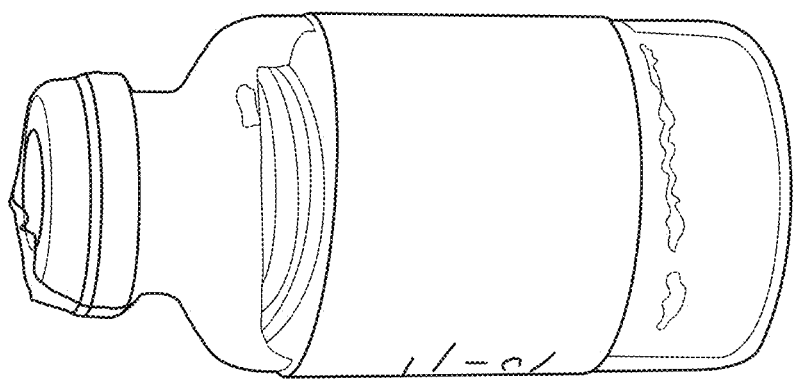
FIGS. 9A and 9B depict SE61 samples after freeze-drying prior to gas refilling.
Figure 9A:
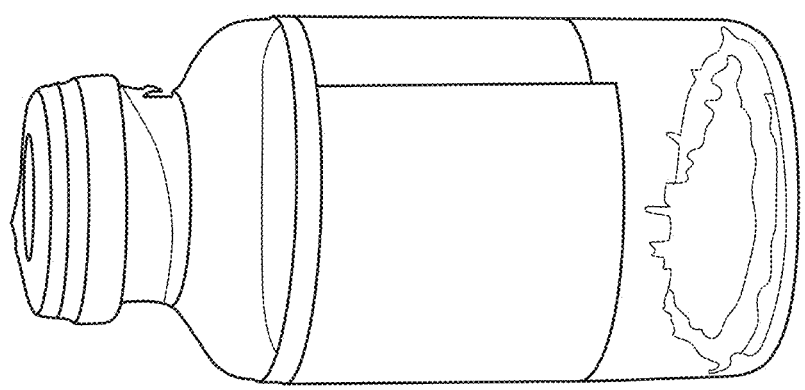

During the drying cycle when samples were subjected to vacuum, frozen SE61 in a 1.8% (w/v) glucose-PBS solution could be observed to bubble and rise in the sample vials. After completion of the freeze-drying cycle, meltback (collapse) of the final dried microbubble cake was also observed (FIG. 9A) compared with intact cake in the 5.0% (w/v) glucose-PBS solution (FIG. 9B). Therefore, the temperature profile of the sample during the drying step was determined, and DSC was conducted on the $SE61_{PFC}$ solutions prior to freeze-drying to determine melt and Tg' properties.

Figure 10:
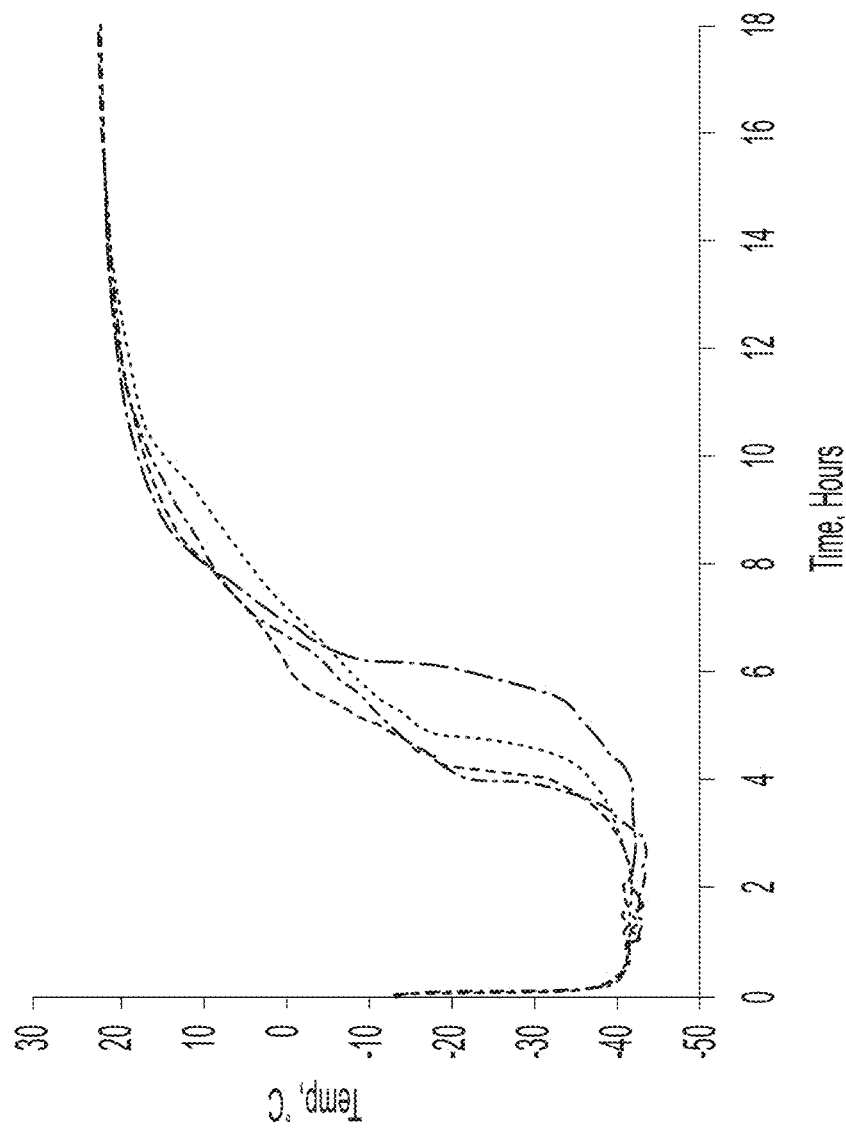
FIG. 10 depicts typical SE61 sample temperatures during freeze-drying.

Typical recorded sample temperatures during freeze-drying are shown in FIG. 10. Samples temperatures were between −15° C. and −20° C. by the end of shelf loading, and then cooled due to sublimation after the application of vacuum, to between −40° C. and −45° C. The samples remained at that temperature until the drying front approached the thermocouples at the base of the vial, about 4-6 hours, rose past 0° C. as the front passed, and leveled off at room temperature once the entire sample had dried, at about 14-16 hours. The reported collapse temperature of −42.7° C. for a 5% glucose solution (Abdelwahed, W.; Degobert, G.; Stainmesse, S.; Fessi, H., Freeze-drying of nanoparticles: formulation, process and storage considerations. Adv. Drug Del. Rev. 2006, 58 (15), 1688-1713), which is the maximum temperature that the product can withstand during primary drying without it melting or collapsing, is very close to the recorded sublimation temperature. For amorphous samples, collapse temperatures are near Tg', which in the case of 5% glucose is −41.4° C. ((Abdelwahed, W.; Degobert, G.; Stainmesse, S.; Fessi, H., Freeze-drying of nanoparticles: formulation, process and storage considerations. Adv. Drug Del. Rev. 2006, 58 (15), 1688-1713). This indicates that a stable freeze-dried product can likely be produced if the Tg' of SE61 solution is similar to that reported for a 5% (w/v) glucose solution of nanoparticles.

Figure 11A:
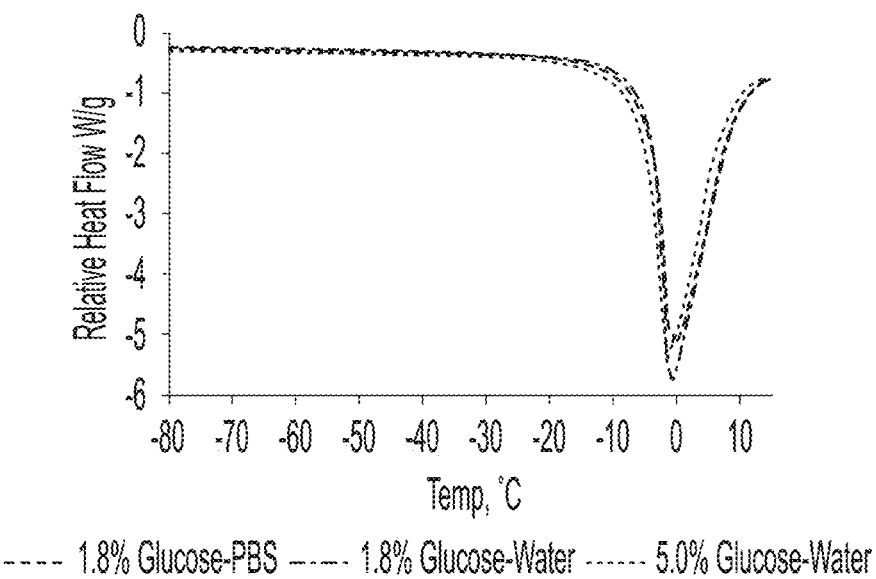
FIGS. 11A and 11B depict differential scanning calorimetry curves of $SE61_{PFC}$ with the three lyoprotectants.
Figure 11B:
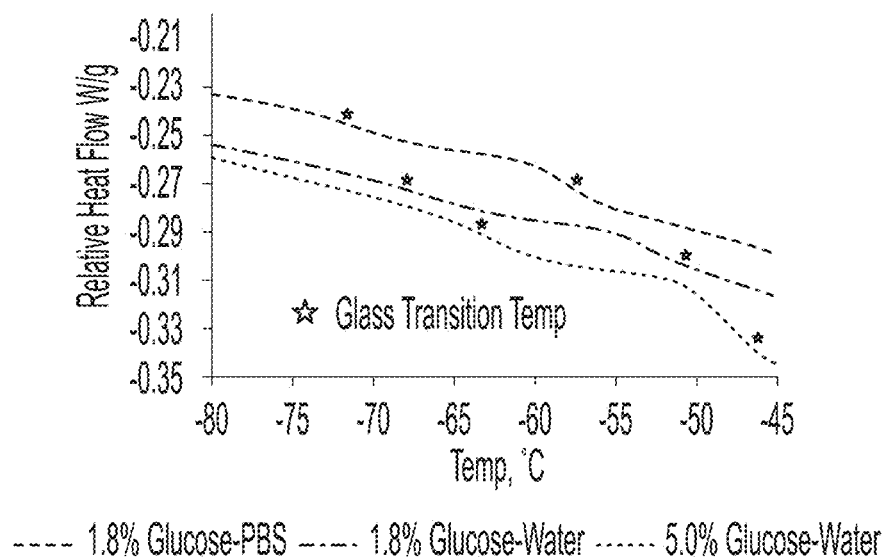

To further investigate the thermodynamic effects of the cryoprotectant, DSC was conducted on $SE61_{PFC}$ in three glucose solutions: 1.8% (w/v) glucose-PBS solution, 1.8% (w/v) glucose-water solution, and in 5.0% (w/v) glucose-water solution. The results are shown in FIG. 11A-11B. The effect of the lyoprotectant composition and concentration on the colligative properties can be seen in the overall DSC graphs (FIG. 11A). While all three samples have melt onsets near −15° C. and have similar melt peaks, the 5% (w/v) glucose-water begins to melt at a lower temperature, while the 1.8% (w/v) glucose-water remains frozen at a slightly higher temperature. Differences of crystallization temperatures due to the different amounts of solutes were also observed during cooling (data not shown), with the PBS solution freezing near −20° C., the 1.8% (w/v) glucose-water solution freezing around −12° C. and the 5.0% (w/v) glucose-water solution in between. This emphasizes that care should be taken during loading onto the freeze-drier to ensure that the temperature remains near or below −20° C. All three glucose solutions showed two thermal transitions (FIG. 11B). SE61 in a 1.8% (w/v) glucose-PBS solution, the lyoprotectant used in the in vivo experiments (Eisenbrey, J. R.; Shraim, R.; Liu, J.-B.; Li, J.; Stanczak, M.; Oeffinger, B.; Leeper, D. B.; Keith, S. W.; Jablonowski, L. J.; Forsberg, F., Sensitization of Hypoxic Tumors to Radiation Therapy Using Ultrasound-Sensitive Oxygen Microbubbles. Int. J. Rad. Oncol. Biol. Physics 2018, 101 (1), 88-96), was found to have a Tg' at −72° C. and at −58° C. Removing salts from the solution by replacing PBS with water, resulted in the measured Tg's increasing to −68° C. and −51° C.

When the concentration of glucose was increased to 5.0% (w/v), the Tg's increased to −64° C. and −47° C. These DSC data clearly show that the Tg' is raised by removing salts and by increasing the glucose concentrations. However, in the absence of salt and with increasing glucose concentration, all three solutions present measured glass transition temperatures lower than the temperature that is maintained by our freeze-drier, which would indicate that collapse might be expected during the drying phase. However, only samples made with glucose-PBS solutions were observed to suffer cake collapse and meltback after drying as glucose-water samples appeared intact (FIG. 11B). Measured glass transition temperatures can be affected by the rate of sample heating and cooling, with faster cooling and slower heating lowering the measured Tg'(Moynihan, C. T.; Easteal, A. J.; De BOLT, M. A.; Tucker, J., Dependence of the fictive temperature of glass on cooling rate. J. Am. Ceramic Soc. 1976, 59 (1-2), 12-16). Thus, the fact that intact samples were produced despite the measured Tg's for both glucose-water solutions being below the recorded sample temperature, and the fact that the measured Tg' for SE61 in 5.0% (w/v) glucose solution was below the reported collapse temperature, can be explained by the fact that the DSC samples were not cooled in the same manner as the SE61 sample freezing methods described above. The DSC analysis was intended to be used for comparison among lyoprotectants and not a definitive measure. The creation of an intact, non-collapsed cake with glucose-water solutions also align with our lab's initial development of the freeze-drying process, which utilized 1.8% (w/v) glucose-water solution (Solis, C.; Forsberg, F.; Wheatley, M. A., Preserving enhancement in freeze-dried contrast agent ST68: Examination of excipients. Int. J. Pharm 2010, 396 (1-2), 30-38).

Shelf-Life Study

Figure 12A:
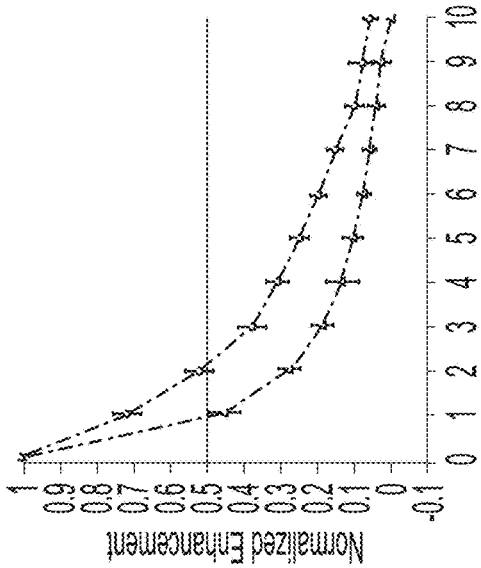
FIGS. 12A-12F depict dose and time response curves for $SE61_{O2}$ at Day 0 and Day 7.
Figure 12C:
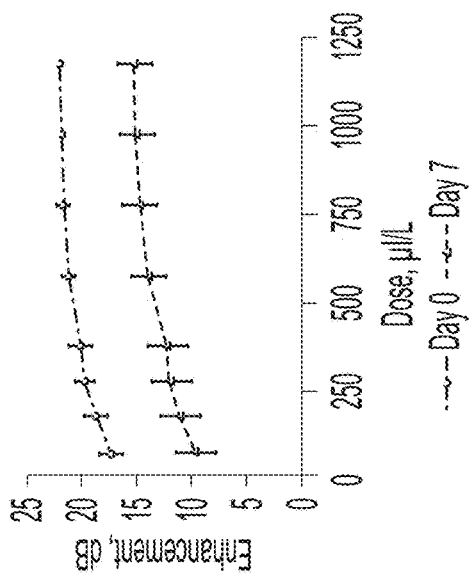
Figure 12B:
Figure 12D:
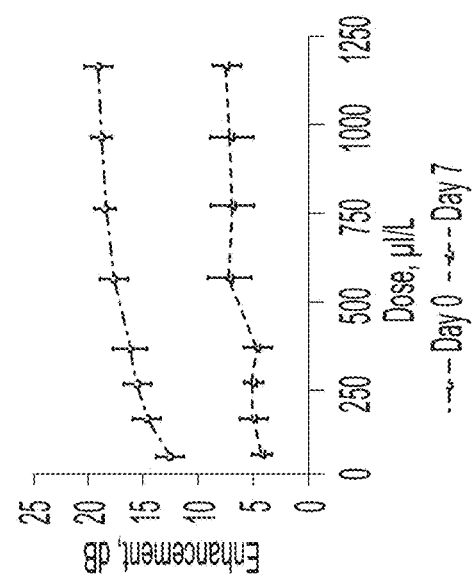
Figure 12F:
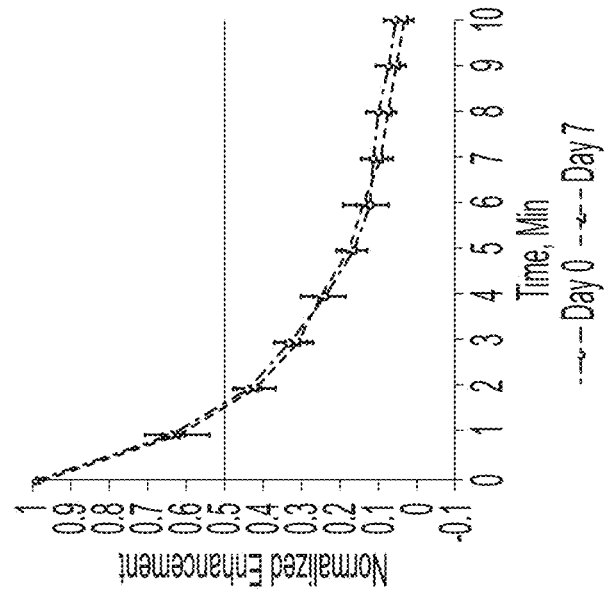
Figure 12E:
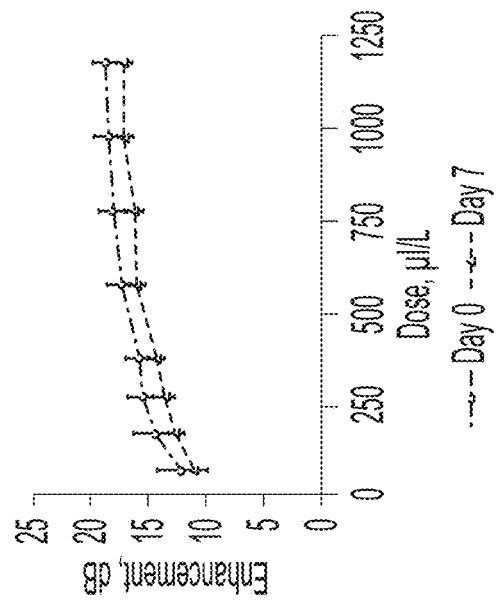

After observing a loss of enhancement due to storage at room temperature, a short term shelf-life study was conducted on $SE61_{O2}$, with dose and time response curves constructed immediately after freeze-drying and after 7 days at room temperature. This study was conducted with $SE61_{O2}$ created with the three lyoprotectant solutions tested by DSC. The acoustical evaluations are given in FIGS. 12A-12F. Curves for $SE61_{O2}$ created with 1.8% (w/v) glucose-PBS (FIGS. 12A and 12B) indicate a significant (p=0.025) drop in the dose response curve of approximately 7-8 dB across the curve, with enhancement at a dose of 580 ml/L dropping from 21.4±0.5 to 14.1±1.6 dB. This loss was also observed in the time response, while not statistically significant (p=0.075), in which at Day 0 the acoustical half-life (defined as the time at which the normalized echogenicity drops 50% of the initial value) was between 2 and 3 minutes, but was approximately 1 for Day 7. This was then repeated with use of 1.8% (w/v) glucose-water (FIGS. 12C and 12D), which was reported to have a stable shelf-life with ST68PFC. As with the PBS solution, removing the salts from the lyoprotectant did not result in initial shelf-life stability of $SE61_{O2}$, with significant decreases in both dose (p=0.006) and time (p=0.011) responses after 7 days. Thus, the addition of PBS to the $SE61_{O2}$ solution was not responsible for the difference in shelf-life compared to ST68PFC. The concentration of glucose was then increased to 5.0% (w/v) (FIGS. 12E and 12F) to match the concentration reported in the literature to successfully stabilize nanocapsules. Although the dose response was slightly lower, no significant differences in the dose (p=0.32) or the time (p=0.89) responses were observed over the 7 days.

Population Dynamics

Figures 1, 13:
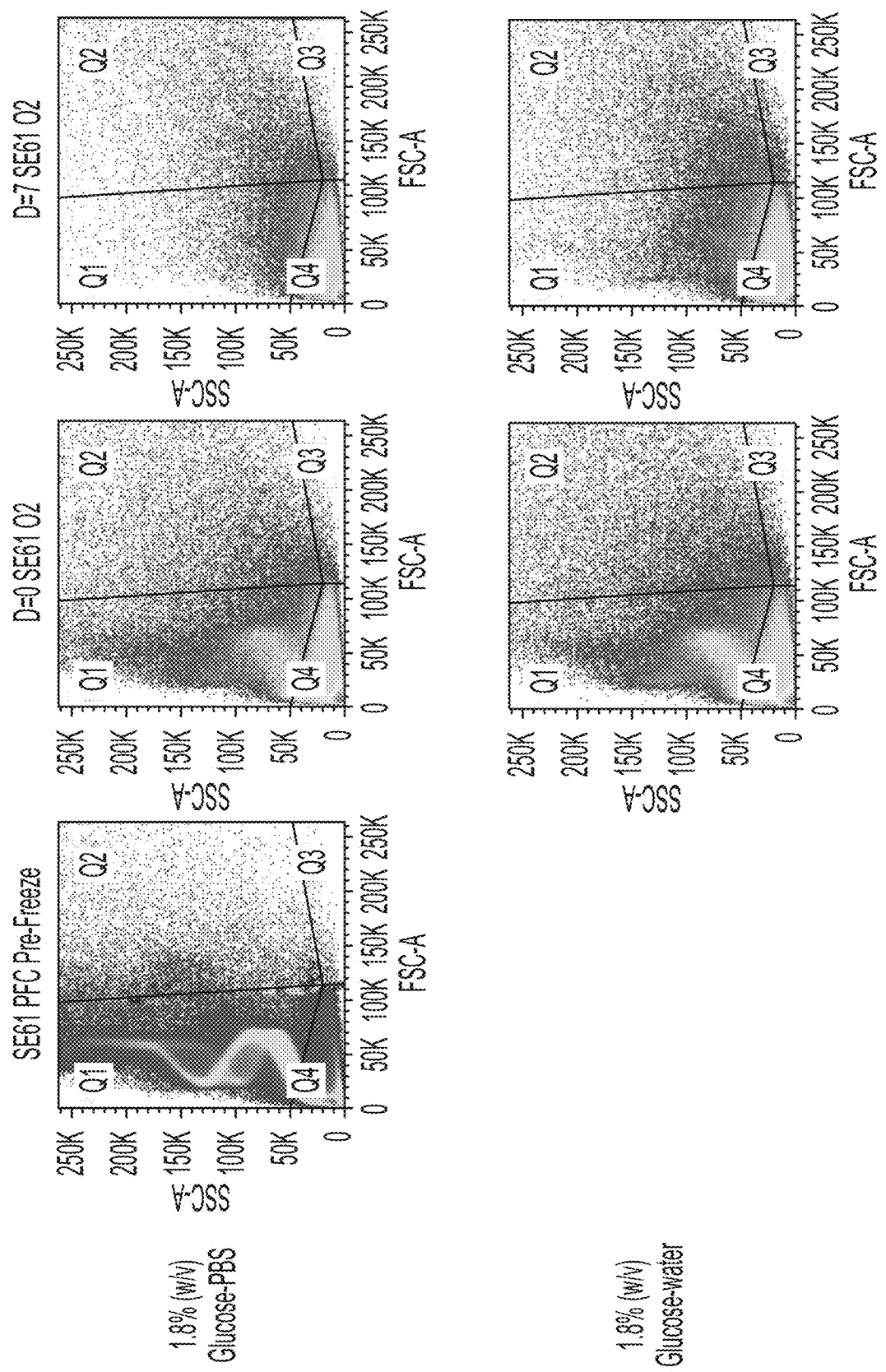
Figures 2, 13:
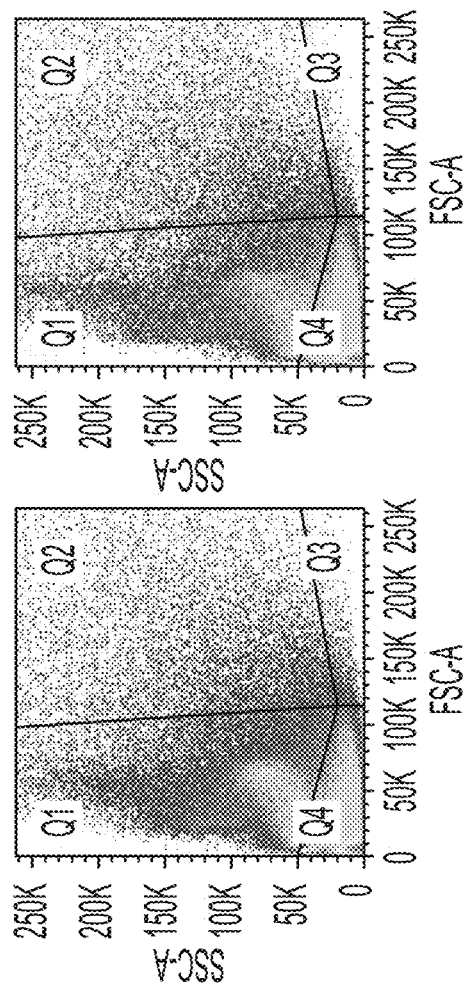

The bubble size was evaluated using dynamic light scattering and bubble count using flow cytometry, for the three different lyoprotectants at Day 0 and at Day 7, which can be found in Table 1 and FIG. 13. The overall size averages for both $SE61_{O2}$ created with 1.8% (w/v) glucose-PBS and 1.8% (w/v) glucose-water lyoprotectants decreased between Day 0 and Day 7, from 2.55±0.53 to 1.79±0.23 μm (p=0.121) and 2.1±0.40 to 1.39±0.26 μm (p=0.046), along with the total microbubble concentration from 17.8±1.2 E+07 to 9.6±0.4 E+07 bubbles/mL (p=0.024) and 22.8±1.9 E+07 to 15.2±0.9 E+07 bubbles/mL (p=0.003). Interestingly, for both the 1.8% (w/v) glucose samples, when analyzed by quadrant, the percent losses of bubbles in quadrant 1 (Q1) were higher than the total percent loss and lower in Q4, indicating a population change in addition to a loss of total bubbles. It is postulated that Q1 contains bubbles with substantial echogenicity while Q4 contains a proportion of smaller, non-echogenic particles. This would also correspond with the reduction in size results at Day 7. Together, this indicates that the loss of enhancement found in the acoustical evaluations for both the 1.8% (w/v) glucose PBS and water samples are due to bubble loss. $SE61_{O2}$ created with 5.0% (w/v) glucose-water differed in that there were non-significant changes in bubble size (1.47±0.22 to 1.42±0.16 p=0.773) and total microbubble concentration (15.3±2.4 E+07 to 11.8±0.7 E+07 bubbles/mL, p=0.070), and the change in each quadrant were similar to the overall, changes indicating that there was not a large change in relative bubble populations. Most importantly, the loss of bubbles in Q1, which is believed to contain mostly echogenic bubbles, was less than 20% compared to over 65% for both the 1.8% (w/v) glucose samples. This indicates that the 5.0% (w/v) glucose-water lyoprotectant is better at stabilizing microbubble acoustical properties by preventing the destruction of the microbubble population.

Stability Studies

Figure 14:
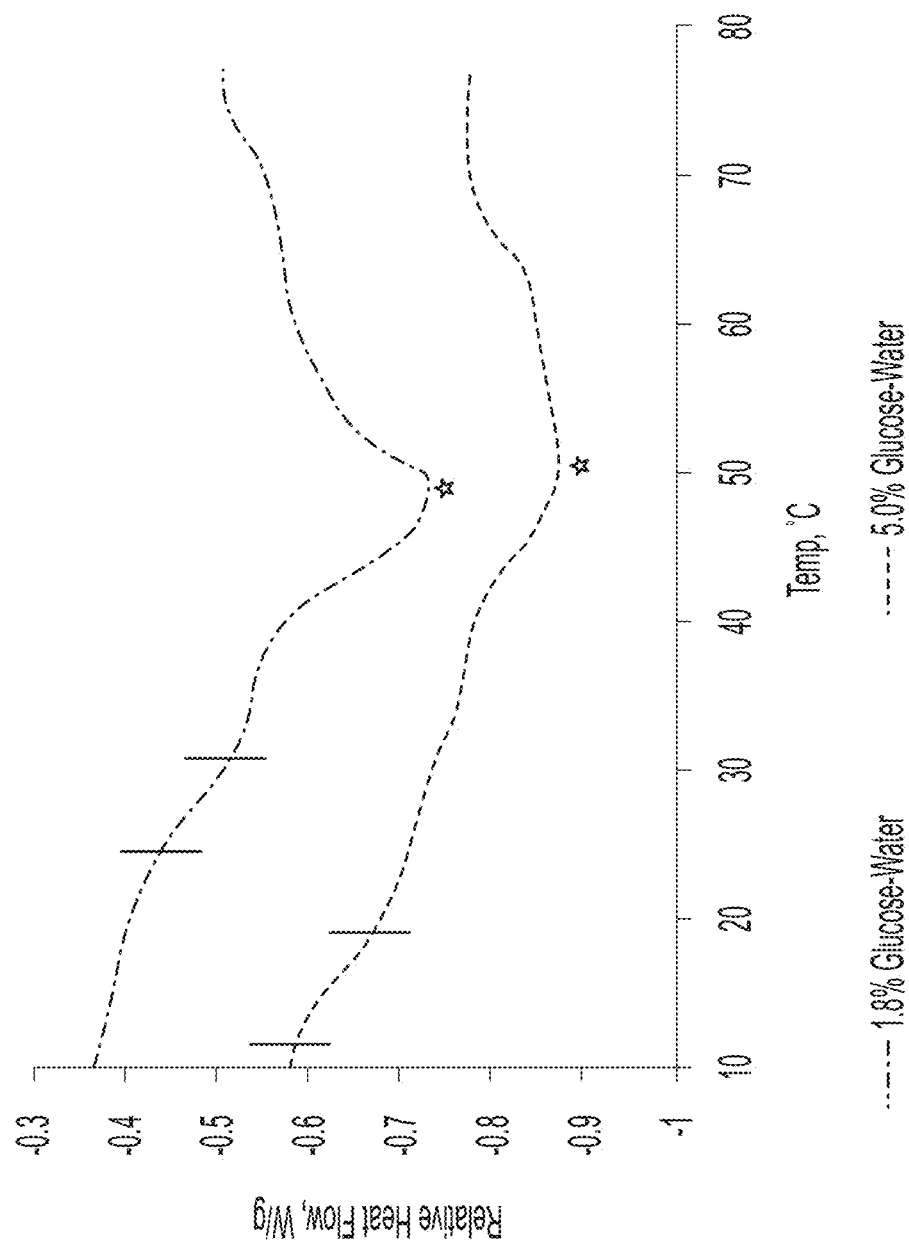
FIG. 14 depicts differential scanning calorimetry curves of dried $SE61_{O2}$ with 1.8 and 5.0% (w/v) glucose. Brackets indicate shift in the Tm, and the star indicates the measured melt temperature.
Figures 1, 15:
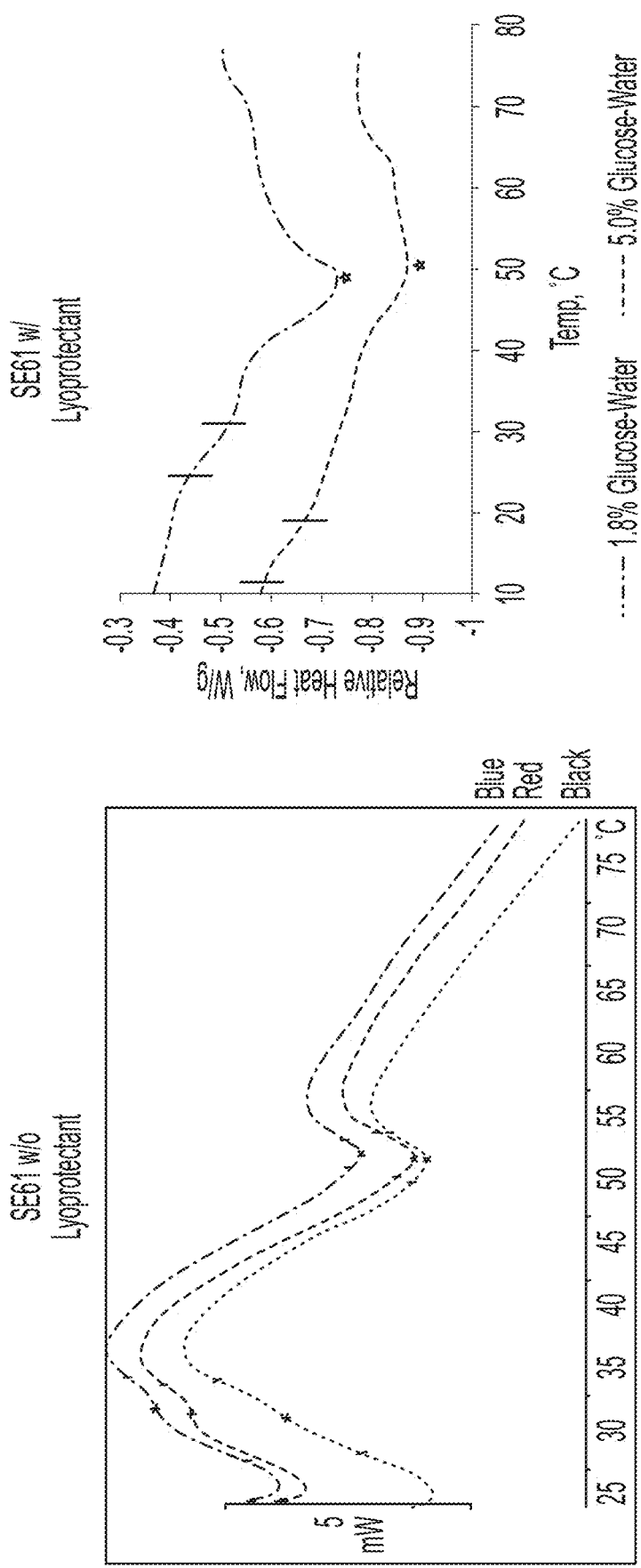

DSC was then conducted on freeze-dried $SE61_{O2}$, found in FIG. 14, to determine why increasing the glucose solution from 1.8 to 5.0% (w/v) improved stability. A comparison of the $SE61_{O2}$ data from FIG. 14 next to $SE61_{O2}$ without lyoprotectant is shown in FIGS. 15-1 and 15-2 to more clearly illustrate the effect of lyoprotectant. Without being bound to theory, one possibility is that the increase in glucose concentration raised the Tg' of the dried glucose, reported to be around 23° C., thus preventing collapse of the dried cake (Simperler, A.; Kornherr, A.; Chopra, R.; Bonnet, P. A.; Jones, W.; Motherwell, W. S.; Zifferer, G., Glass transition temperature of glucose, sucrose, and trehalose: an experimental and in silico study. J. Phys. Chem. B 2006, 110 (39), 19678-19684). Another possibility is that a phase transition exists between a liquid crystalline and gel phase, and that increasing the glucose solution concentration lowers the observed Tm, as is the case in liposomes. For $SE61_{O2}$ freeze-dried in 1.8% (w/v) glucose-water, a phase transition can be seen between 24.4 and 31.3° C. along with a melt peak of 48.9° C. While $SE61_{O2}$ freeze-dried in 5.0% (w/v) glucose-water had a similar melt peak of 50.3° C., the phase transition has shifted lower, between 11.6 and 19.5° C., supporting the theory that a phase transition exists between a liquid crystalline and gel phase. Without being bound to theory, this shifting phase transition is likely associated with a change in the TPGS phase, while the higher peak is near the melt temperature of SPAN® 60. This would be in agreement with the microbubble shell being polycrystalline with multiple phases. Increasing the concentration of glucose to 5.0% (w/v) shifts the transition temperature from above to below room temperature. This would prevent the sample from going through the transition during rehydration. However, if this was solely the cause of microbubble disruption, differences in bubble integrity immediately after freeze-drying would be expected between glucose concentrations. One possibility is that $SE61_{O2}$, unlike liposomes, can remain intact during a phase change cause by hydration, but is more stable during storage in the liquid crystal phase. $SE61_{O2}$ in a gel phase would likely be more rigid and fragile, and less compatible with the glassy nature of the freeze-dried cake.

CONCLUSIONS

This study shows the important influences of the many different steps in freeze-drying on the stability of the microbubble interface. A slower freezing rate of the microbubbles results in better preservation of the acoustical properties after drying, and can be achieved using a −20° C. bath. This slow freeze results in larger ice crystals being formed, allowing for a higher concentration of glucose around the microbubble, which becomes even more important with higher concentration of sugars. It has also been shown that the ionic strength of the suspending medium and the concentration of the lyoprotectant determines the Tg' of the frozen sample, which in turn determines at what temperatures samples can be dried without collapse. The addition of PBS to the lyoprotectant solution causes dried microbubble cake collapse due to a decrease of Tg' below Applicants' sample cooling abilities. Most importantly, it has been shown that the shelf stability of $SE61_{O2}$ microbubble can be enhanced by increasing the glucose concentration to 5.0% (w/v). This increase lowers the microbubbles emulsifier's Tm, with stable microbubbles existing in a liquid crystal phase at room temperature. The changes in properties compared to $SE68_{PFC}$ are due to the differences in molecular structure of the surfactants used to stabilize the bubble interface, with TPGS replacing TWEEN® 80. While the use of glucose to achieve the shift in Tm may be unique to SE61, the shift in Tm is likely important for the stable freeze-drying of any stabilized microbubble shell.

INCORPORATION BY REFERENCE

The disclosures of each and every patent, patent application, and publication cited herein are hereby incorporated herein by reference in their entirety.

EQUIVALENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for annealing surfactant-stabilized microbubbles, the method comprising:
    preparing vials comprising a mixture comprising surfactant-stabilized microbubbles;
    passing the vials in and out of liquid nitrogen ($LN_2$) until the mixture is frozen;
    holding the vials at −20° C.;
    placing the vials on a cooled shelf of a lyophilizer, wherein the cooled shelf has a temperature between about −10° C. to about −30° C.;
    freeze-drying the vials in the lyophilizer; and
    capping the freeze-dried vials.

2. The method of claim 1, wherein the mixture further comprises a lyoprotectant.

3. The method of claim 2, wherein the lyoprotectant comprises one or more selected from the group consisting of: sugar, polymer, surfactant, and combinations thereof.

4. The method of claim 3, wherein the lyoprotectant comprises the sugar, and wherein the sugar comprises one or more selected from the group consisting of: glucose, trehalose, sucrose, dextran and mannitol.

5. The method of claim 3, wherein the lyoprotectant comprises the polymer, and wherein the polymer comprises one or more selected from the group consisting of poly (vinylalcohol) (PVA) and poly (vinylpyrrolidone) (PVP).

6. The method of claim 3, wherein the lyoprotectant comprises the surfactant, and wherein the surfactant comprises polyethylene glycol (PEG).

* * * * *